(12) United States Patent
Lehmann et al.

(10) Patent No.: US 11,498,047 B2
(45) Date of Patent: Nov. 15, 2022

(54) DEVICE FOR THE ENERGY-OPTIMIZED PRODUCTION OF FLUID EDDIES IN A REACTION CHAMBER

(71) Applicant: EMCO WATER PATENT GMBH, Lingen (DE)

(72) Inventors: Jörg Lehmann, Lingen (DE); Olaf Linden, Gladbach (DE)

(73) Assignee: EMCO WATER PATENT GMBH, Lingen (DE)

( * ) Notice: Subject to any disclaimer, the term of this patent is extended or adjusted under 35 U.S.C. 154(b) by 940 days.

(21) Appl. No.: 16/325,400

(22) PCT Filed: Aug. 24, 2016

(86) PCT No.: PCT/EP2016/069983
§ 371 (c)(1),
(2) Date: Feb. 14, 2019

(87) PCT Pub. No.: WO2018/036623
PCT Pub. Date: Mar. 1, 2018

(65) Prior Publication Data
US 2019/0193046 A1  Jun. 27, 2019

(51) Int. Cl.
| | |
|---|---|
| *B01J 19/24* | (2006.01) |
| *A61L 2/20* | (2006.01) |
| *A61L 12/00* | (2006.01) |
| *B01J 19/00* | (2006.01) |
| *B01D 21/26* | (2006.01) |
| *B01J 19/26* | (2006.01) |

(52) U.S. Cl.
CPC .......... *B01J 19/2405* (2013.01); *A61L 2/202* (2013.01); *A61L 12/00* (2013.01); *B01D 21/265* (2013.01); *B01J 19/006* (2013.01); *B01J 19/26* (2013.01)

(58) Field of Classification Search
CPC ...... B01J 19/2405; B01J 19/006; B01J 19/26; A61L 2/202; A61L 12/00; B01D 21/265
USPC .......................................................... 422/28
See application file for complete search history.

(56) References Cited

FOREIGN PATENT DOCUMENTS

WO      WO-0187473 A1 * 11/2001 ............ B01F 5/0057

* cited by examiner

*Primary Examiner* — Huy Tram Nguyen
(74) *Attorney, Agent, or Firm* — John Alumit

(57) ABSTRACT

The invention relates to a device consisting of a reactor facility for the flow dynamics treatment of fluid or gaseous media or mixtures of the two. In the context of this invention, flow dynamics treatment means the energy-optimised production of at least one rotating fluid eddy together with an eversion of the at least one fluid eddy and the bursting open of organic constituents dissolved in the fluid medium with inner cell pressure (Turgor). The guided fluid eddy is treated, cleaned and disinfected in the reactor facility according to the invention. The invention further relates to a method for the flow dynamics treatment of fluid media in the reactor facility according to the invention.

11 Claims, 5 Drawing Sheets

DEVICE FOR THE ENERGY-OPTIMIZED PRODUCTION OF FLUID EDDIES IN A REACTION CHAMBER

The subject of the present invention is a device in the form of a flow dynamic reactor facility for receiving a fluid medium. The subject of the present method is the energy-optimized production and flow dynamics treatment of at least one guided fluid eddy in a reaction chamber.

In it, the fluid eddy is produced by putting a fluid medium into rotation in a reaction chamber and receiving it in an outlet pipe by a directional change by means of diversion. The outlet pipe can produce a Venturi effect. The guided volume flow of the fluid medium, at the latest when it exits the reactor facility, forms a fluid eddy.

Conventional devices and reaction containers as well as methods for flow dynamics treatment of fluid media are known for instance from AT 272 278, DE 195 25 920 A1, DE 101 14 936, or EP 1 294 474 B2.

In AT 272 278 and DE 101 14 936 A1, fluid media are delivered to a reaction chamber and set into rotation by means of its geometric form. In the process, the speed of the rotating fluid medium initially decreases because of the geometric shape of the reaction chamber. Next, it increases again as a consequence toward the floor region at the lower end of the reaction chamber. The fluid medium moving in rotational fashion to the floor region of the reaction chamber is conducted at the lower end of the reaction chamber, counter to the former flow direction, to a longitudinal axis and steered upward. Next, it is caught in an outlet pipe and leaves the reaction chamber while rotating, forming a hollow eddy. In the floor region of the reaction chamber there are openings along the longitudinal axis or in the immediate vicinity thereof. As a result, via the hollow eddy sink, which at its core generates a negative pressure, additional fluid media can be aspirated.

In DE 195 25 920 A1, an expansion of the device of AT 272 278 is described. In it, the fluid medium to be cleaned flows alternatingly in ascending and falling fashion through inlet tubes communicating with one another. After that, downstream of the outlet from the reaction chamber, the flowing fluid medium is conducted into a tube labyrinth for sedimentation or for collecting the thickened waste products.

A disadvantage of these devices is the complicated embodiment, the unwieldiness for an intended technical use, the lack of flexibility and adjustability of the components or parts of the reactor facility, and the resultant poor replicability of the results.

In EP 1 294 474 B2, the reaction chamber of the reactor facility is constructed with a heart-shaped or pear-shaped cross section. The outlet pipe, which is adjustable and extends into the floor region, along the longitudinal axis of the reaction chamber is embodied in the region near the mouth as a nozzle for attaining the Venturi effect.

The fluid medium is added to the reaction chamber via at least one delivery opening located tangentially to the reaction chamber and moves, accelerated and in rotation, as a fluid eddy in the downward flow direction around the outlet pipe. As a result of the fluid passage, which in the lower housing region diverts the volume flow, which maintains its absolute rotary direction, rotationally toward the longitudinal axis, a region of rotating volume flows that rub against one another is created, each at high speeds. The result of the relative speed attained and the pronounced friction is mechanical comminution and destruction of entrained or dissolved substances.

The delivery opening here is larger than the smallest cross section of the nozzle in the region of the outlet pipe near the mouth, as a result of which a dynamic pressure is created. Thus, along with the fluid eddy formation, which generates a vacuum in the core of the eddy, an additional vacuum effect in the translational direction is due to of a Venturi effect. The Venturi effect is in turn based on the Bernoulli equation $$p_{ges.} = p_0 + \frac{p}{2}c^2 + pgh,$$

in which $p_0$ is the static pressure, which is present on all sides in the flow;

$$\frac{p}{2}c^2$$

is the dynamic pressure, which is equivalent to the kinetic component of the energy with the flow speed c, and pgh represents the geodetic pressure component. The flow speed c in turn results from the product of the angular speed $\omega$ having the radius r, which extends in longitudinal section from the outermost point of the reaction chamber toward the outer wall of the outlet pipe ($c=\omega \cdot r$). The angular speed $\omega$ below is also equivalent to the rotary speed of the fluid medium.

Furthermore, because of the high centrifugal force and because of the friction, the structure of the fluid medium varies such that in the case of liquid fluid media, a change in the surface tension and a viscosity ensues. In this state, the fluid medium enters, rotating, into the inlet opening of the outlet pipe. As a result, an eddy flow develops, with an eddy core at high speed, which because of the laws of flow dynamics generates a vacuum in its middle. The nozzle for attaining the Venturi effect, which is present in the lower region near the mouth of the outlet pipe, causes this vacuum region, given equivalent flow speed, to be superimposed and thus intensified by the generation of an additional vacuum. The resultant negative pressure can according to Bernoulli's equation amount to absolutely <10 mbar. By means of pressure and negative pressure as well as the associated eddy formation, very high mechanical forces in the fluid medium are liberated. They cause a change in the structure of the fluid medium, to the extent of a slight surface tension.

Organic components entrained in the fluid medium, such as bacteria and germs, burst open mechanically because of their own internal cellular pressure (turgor) in the negative-pressure range. The organic residues are carried through the altered pressure region to a chemical reaction, based on the thermal state equation of ideal gases, $p \cdot V = m \cdot R \cdot T$. Entrained strains can be carried to reaction, depending on the necessary reaction enthalpy, in the negative-pressure range. The result is oxidation of the fluid medium with oxidation means such as oxygen or by means of aspirated oxygen from the ambient air. This happens as a function of the energy input in the system with other oxidizable substances as well—however, there, a limit is set physically in accordance with the thermal state equation of ideal gases.

In EP 1 294 474 B2 and DE 195 25 920 A1, the reaction chamber is embodied geometrically such that the rotating fluid medium experiences an acceleration by tapering of the reaction chamber in the flow direction from the delivery opening to the fluid passage and finally to the lower region, near the mouth, of the outlet pipe.

A disadvantage of these inventions is the high amount of energy required to put the fluid medium into rotation, which has to do with the form and embodiment of the reaction chamber. Associated with this is the poor commercial value for generating the negative pressure and what, despite a surprisingly good mode of operation, is a limited enthalpy input to the reaction of chemical compounds or organic strains without their own cellular pressure (turgor), as is the case with yeasts and fungi, for example.

In the method, and the associated facility embodiment, described in EP 1 294 474 B2, for producing the rotation of the fluid medium considerable quantities of flow energy are needed, since losses occur from unwanted eddies that arise because of fluid friction in the reaction chamber.

The losses of flow energy can amount to more than 20%. In the for instance available input-side pump pressure of 6 bar, in the entire reactor facility, depending on the facility embodiment, only 2 to 3 bar are available on the outlet side. If furthermore one observes that at least 1 bar is needed to generate the negative pressure in a nozzle for attaining the Venturi effect, and pressure is also needed on the surfaces because of fluid friction, the pressure losses from fluid friction range from at least 20-30%. Furthermore, as a result of the unwanted eddies, major cavitation regions occur in the reaction chamber. The eddies can lead to unwanted abrasion of the walls of the reaction chamber as well as to destruction of regions of the reaction chamber or the nozzle, as the mechanically weakest member.

The present invention has the object of proposing an advantageous device as well as an advantageous method for operating this device, which reduce the losses of flow energy in the reaction chamber, specifically by means of a geometric and rotationally symmetrical design, optimized in terms of flow, of the reaction chamber as far as the inlet opening of the outlet pipe. Furthermore, by means of the device of the invention, with the same energy consumption a greater acceleration of the fluid medium in the reaction chamber is to be attained. In addition, the formation of unwanted eddies, generated by fluid friction, in the reaction chamber is to be reduced.

As a result of the varying pressure conditions in the reaction chamber based on eddy formations, it is intended by the proposed method that the breakdown sought and the mechanical destruction and comminution of foreign substances dissolved in the fluid medium will be effected more efficiently because of the available frictional and centrifugal forces.

As a result, fluid media are to be cleaned and processed faster, more economically, in a more space-saving and environmentally friendly way, and with greater power.

It is furthermore an object of the invention to use the device and the method of the invention as well as a device for performing the method.

This object is attained with the features recited in claims 1 and 10. Advantageous features of the device of the invention, the method of the invention, and the use of the invention, are recited in claims 2 through 9 and 11 through 13.

According to the invention, the object is attained by a reactor facility for flow dynamics treatment of fluid media based on mechanical, physical, and chemical processes.

The object is furthermore attained by a flow dynamic reactor facility for receiving a fluid medium for producing at least one guided fluid eddy. The reactor facility includes a housing and an outlet pipe, and the housing, by means of the inner walls in contact with the fluid, forms a fluid-carrying hollow chamber that is rotationally symmetrical about a longitudinal axis and that will hereinafter be called a reaction chamber. The reaction chamber is split in the flow direction of the fluid medium into an upper and a lower part. The upper part of the reaction chamber has a top face, a bottom face, and a transition region from the top to the bottom face. Furthermore, the upper part of the reaction chamber in the transition region from the top to the bottom face has a maximum radius, specifically with reference to the outer wall of the outlet pipe. In the transition region from the top face to the bottom face, there is at least one delivery opening, located tangentially to the jacket face of the upper part of the reaction chamber, specifically with a fluid inlet region adjoining in the flow direction. The top and bottom face each have a setting angle to the longitudinal axis of 80° to 115°. The lower part of the reaction chamber extends in the flow direction at a spacing z from the transition from the bottom face to the lower boundary of a curved floor region. In this floor region, there is a geometrically ascending-shaped fluid passage, which diverts the fluid medium into an inlet opening of the outlet pipe. Furthermore, the outlet pipe coincides in its longitudinal axis with the longitudinal axis of the rotationally symmetrical reaction chamber. The inlet opening of the outlet pipe is located at a spacing a to what in the flow direction is the lower boundary of the curved floor region.

A fluid medium is introduced into the reaction chamber. Fluid media and fluids in the sense of the invention are liquid and/or gaseous substances and/or mixtures of liquid and/or gaseous substances.

Preferably, the fluid medium is a liquid. In one embodiment, at least one pure liquid is delivered as a fluid medium to the reactor facility. In a further embodiment, more than one liquid is delivered as a fluid medium to the reactor facility. Especially preferably, the fluid medium is an aqueous liquid or aqueous solution, or in other words contains water.

In a further embodiment, a mixture of at least one liquid and at least one gas is delivered to the reactor facility. In a further embodiment, more than one mixture of at least one liquid and at least one gas is delivered to the reactor facility.

In an alternative embodiment of the invention, at least and exclusively one gaseous substance or one gaseous mixture is treated, as a fluid medium, in the reactor facility. In a particular embodiment, at least one gas is delivered to the reactor facility.

In the reaction chamber, the at least one guided fluid medium or the at least one guided fluid eddy formed is treated using flow dynamics. The term flow dynamics treatment of the fluid medium in the flow dynamic reactor facility of the invention is understood to mean that the fluid medium is guided as a volume flow via at least one delivery opening and one fluid inlet region, adjoining it in the flow direction, into the reactor facility. The flow direction always refers to that of the fluid medium. As a result of the geometry and design of the reaction chamber, at least one guided fluid eddy is formed. This is done with an eddy eversion of the at least one fluid eddy and the burst open of organic components, dissolved in the fluid medium, with internal cellular pressure (turgor). The at least one guided fluid eddy generated is thus treated using flow dynamics in the reactor facility, and in the process is processed, cleaned and disinfected.

The flow dynamics treatment of the at least one guided fluid eddy is achieved by means of the reactor facility of the invention and method of the invention for operating that reactor facility. As a result of the flow dynamics treatment of the at least one fluid eddy generated, the conversion and/or mechanical and physical destruction and/or radicalization of chemical substances or microorganisms present in the fluid medium preferably takes place.

By the geometry and design of the reactor facility of the invention, and in particular of the reaction chamber, and very particularly of the upper part of the reaction chamber, it is advantageous that less energy needs to be employed, or flow energy is saved and less pressure is needed in order to accelerate a fluid medium. On the other hand, for the same energy consumption, higher rotary speeds of the fluid medium and thus a greater acceleration and efficiency of the reactor facility are ensured. It is on this that the improved method of the invention is based regarding the destruction and comminution of germs, for example, since a greater rotary speed of the fluid eddy is brought about in the reactor facility of the invention.

The reactor facility includes a plurality of components and parts, such as a housing and an outlet pipe, which will be discussed in greater detail below.

The housing consists of a stable material and a body that is hollow in the interior. The housing, by means of the inner walls in contact with fluid, forms a hollow chamber that is rotationally symmetrical about a pivot axis and that will hereinafter be called the reaction chamber. The reaction chamber is thus rotationally symmetrical to the pivot axis. The pivot axis of the reaction chamber will hereinafter be called the longitudinal axis.

All the details recited below regarding the components and parts of the reactor facility refer always to one-half of the reactor facility in longitudinal section. The construction of the second half of the reactor facility on the other side of the longitudinal axis is, however, the same, since the reactor facility is embodied mirror-symmetrically in longitudinal section.

The outer walls of the housing can assume an arbitrary geometrical form. Preferably, the housing is embodied rotationally symmetrically.

In longitudinal section of the reactor facility, an imaginary center plane is located horizontally (that is, perpendicularly to the longitudinal axis). In one embodiment, the center plane extends through the upper part of the housing and of the reaction chamber. In a further embodiment, the center plane extends through the upper part of the housing and the reaction chamber. In a preferred embodiment, the center plane extends through the center points of the fluid inlet region that in the flow direction adjoins the at least one delivery opening.

The housing, in the installed state, is split relative to this center plane into an upper part and a lower part. The upper part of the housing in the installed state is located above the center plane, and the lower part of the housing is attached below the center plane in the flow direction of the fluid medium.

The term flow direction of the fluid medium is understood to be the flow direction of the fluid medium guided into the reactor facility. In the installed state, at the lower boundary of the floor region of what in the installed state is the lower part of the reaction chamber, the fluid medium flows downward and at the fluid passage is diverted upward (contrary to its original direction) into the inlet opening of the outlet pipe. In one embodiment, the fluid medium leaves the reactor facility through the outlet opening of the outlet pipe, at a higher point in the installed state than where it entered the reactor facility through the at least one delivery opening.

In one embodiment, the housing includes at least two openings. The at least two openings include one opening for an inlet pipe for the medium inflow and one opening, located in the upper part of the housing centrally along the longitudinal axis, for an outlet pipe for the medium outflow. In a further, especially preferred embodiment, the housing furthermore also more than one opening for a plurality of inlet pipes and media inflows, for instance, two, three, four or more openings.

In a further preferred embodiment, the housing includes a further opening. This opening represents an opening, located centrally along the longitudinal axis, in the installed state in the lowermost part of the housing for introducing a fluid passage.

Advantageously, the housing has at least one opening for the outlet pipe, at least one opening for introducing a fluid passage, and at least one opening for an inlet pipe.

As a result, more than one fluid medium can be conducted into the upper part of the reaction chamber, and less force is used for introducing the volume flows into the reaction chamber. The volume flows can derive from the pipelines of a main inlet or multiple inlet lines. The volume flows can furthermore consist of the same fluid medium, or different fluid media.

The reaction chamber can assume various geometries. In a very particularly preferred embodiment, the reaction chamber is formed rotationally symmetrically.

The reaction chamber that is rotationally symmetrical about a longitudinal axis is shaped by the inner walls of the housing. In one embodiment, the inner walls of the housing are in contact with the fluid medium. The inner walls of the housing that are in contact with the fluid medium will hereinafter be called walls of the fluid-carrying reaction chamber. The reaction chamber is split, in the flow direction of the fluid medium, into an upper part and a lower part.

The reaction chamber receives the fluid medium that is flowing in through the at least one delivery opening. The fluid medium is conducted as a flow, hereinafter also called volume flow, through the at least one delivery opening into a fluid inlet region in the upper part of the rotationally symmetrical, fluid-carrying reaction chamber and in its further course forms a fluid eddy.

The choice of flow speed depends on the particular properties of the fluid medium and can be ascertained from the strength of the covalent bond and/or the consistency of the molecules. Advantageously, a high speed is chosen for introducing the fluid medium into the upper part of the reaction chamber.

Since the reaction chamber is formed by the inner walls, in contact with the fluid, of the housing, it, analogously to the housing, also has the openings of the housing. The reaction chamber therefore includes at least two openings: one opening for the inlet pipe, which in section with the jacket face of the upper part of the reaction chamber forms a tangentially located delivery opening for the medium inflow, and one opening in the upper part of the reaction chamber along the opening located centrally for the outlet pipe to the media exit. In a further especially preferred embodiment, the reaction chamber furthermore has more than one delivery opening, for instance two, three, four or more delivery openings.

The reaction chamber and the openings for the media flow and for the media exit are designed and located relative to one another in such a way that in the fluid medium to be treated, upon flowing through the reaction chamber from the at least one delivery opening to the outlet opening, the greatest possible shear stresses are produced by friction of the individual flow layers with one another and with the walls of the reaction chamber.

In a preferred embodiment, the reaction chamber has a further opening. This opening represents an opening, located centrally to the longitudinal axis, on the lower boundary of the floor region of the reaction chamber for introducing a fluid passage.

Very preferably, the reaction chamber has at least one opening for the outlet pipe, at least one opening for introducing a fluid passage, and at least one delivery opening.

Preferably, the reaction chamber has two delivery openings. As a result, preferably two or more than two volume flows are introduced into the reaction chamber. The speed of the volume flows here should be selected such that from a flow technology standpoint a turbulent boundary layer can develop and that the volume flows have a high speed difference. Preferably, a combination of translational motion and simultaneous rotary motion is chosen such that the volume flows touch one another.

In one embodiment, all the walls of the reaction chamber are in contact with the fluid medium introduced through the at least one delivery opening. In an alternative embodiment, only a portion of the walls of the reaction chamber are in contact with the fluid medium introduced through the at least delivery opening.

The reaction chamber in the installed state is split along the longitudinal axis in the flow direction into an upper part and a lower part, which are each rotationally symmetrical. According to the invention, the upper part of the reaction chamber is understood to be that part in which the fluid medium is introduced through the at least one delivery opening. The upper part of the reaction chamber, viewed along a center plane, extends from the at least one delivery opening for the medium inflow to an outer wall of the outlet pipe.

In one embodiment, the upper part of the reaction chamber has a top face and a bottom face, which are each formed by the walls of the reaction chamber.

The top face includes the surface that from the wall of the upper reaction chamber extends from the upper region, in the installed state, of the at least one delivery opening and the adjoining fluid inlet region, to the termination with the outer wall of the outlet pipe. The bottom face is formed by the wall of the upper reaction chamber and includes the surface which extends from what in the installed state is the lower region of the at least one delivery opening and the adjoining fluid inlet region to the lower part of the reaction chamber.

Preferably, the spacing which extends from the bottom face of the upper part of the reaction chamber to the outer wall of the outlet pipe along a plane parallel to the center plane is defined as the radius. Furthermore, the disadvantageous pressure losses in EP 1 294 474 B2 are circumvented because in the present invention, the radius in the flow direction remains constant or decreases continuously. In a preferred embodiment, $r_1$ is markedly greater than the spacing b between the bottom and the top face.

Furthermore, the upper part of the reaction chamber has a transition region from the top face to the bottom face. Preferably, the transition region from the top to the bottom face in longitudinal section of the reactor facility represents a circular sector or ellipsoid sector. In a further embodiment, the transition region can have different geometric forms from the top face to the bottom face. The transition region from the top to the bottom face furthermore, in longitudinal section of the reactor facility, represents the farthest point of the reaction chamber away from the outer wall of the outlet pipe.

The spacing from the transition region from the top face to the bottom face in the upper part of the reaction chamber to the outer wall of the outlet pipe along the center plane represents the maximum radius of the reaction chamber and will hereinafter be called the maximum radius $r_{max}$. Here, $r_{max}$ in one embodiment extends along the center plane, that is, from the transition region between the top and bottom face of the upper part of the reaction chamber through the center point of the fluid inlet region to the outer wall of the outlet pipe. In accordance with Bernoulli's equation and the principles of eddies, the vapor pressure of the fluid medium in the vicinity of $r_{max}$ Rotary momentum formula $L=\dot{m}cr$ with the mass flow $\dot{m}$ cannot be achieved via the attained angular or rotary speed. For the mass flow, $\dot{m}=\dot{V}\cdot\rho$ applies, where $\dot{V}$ represents the volumetric flow and $\rho$ represents the density of the fluid medium. For a constant mass flow $\dot{m}$ and a constant rotary momentum L, again, the rotary speeds and thus the angular speed w of the fluid medium ascend markedly upon a reduction of $r_{max}$.

Preferably, the upper part of the reaction chamber in the transition region from the top face to the bottom face has at least one delivery opening, entering tangentially to the cross section of the jacket face of the upper part of the reaction chamber, as a result through which delivery opening the fluid medium is conducted into the reaction chamber.

In a preferred embodiment, the at least one delivery opening is thus located at the most pronounced spacing $r_{max}$ of the upper part of the reaction chamber between the transition region between the top and bottom face and the outer wall of the outlet pipe is located along the center plane, as a result of which advantageously a longer acceleration path for the fluid medium is furnished in the upper part of the reaction chamber.

The at least one delivery opening is adjoined in the flow direction of the fluid medium by a fluid inlet region in the upper part of the reaction chamber, which region, preferably in longitudinal section of the reactor facility, has a circular surface with a diameter $d_z$.

In a preferred embodiment, the top face and the bottom face of the upper part the reaction chamber, in the flow direction from the transition region from the top to the bottom face up to the transition of the bottom face with the lower part of the reaction chamber, have a maximally constant spacing b from one another. The maximally constant spacing b of the top to the bottom face to one another is preferably here from one to three times the diameter $d_z$ of the fluid inlet region ($b \leq 3\ d_z$). If the spacing b is constant, then the constant spacing b is simultaneously equivalent to the maximum spacing $b_{max}$ between the top and bottom face (viewed in longitudinal section of the reactor facility).

Very preferably, for an advantageous acceleration of the fluid medium, the constant spacing of the top to the bottom face is equivalent to the single diameter $d_z$ of the fluid inlet region ($b=d_z$), as a result of which the upper part of the reaction chamber represents a relatively slender and flat region for the inflowing fluid medium. In the case, the upper part of the reaction chamber in longitudinal section of the reactor facility has a disklike or platelike appearance.

In an alternative preferred embodiment, the top and bottom face in the flow direction of the fluid medium, from the transition region from the top to the bottom face to a transition of the bottom face to the lower part of the reaction chamber, have a decreasing spacing b from one another. Preferably, the spacing b in the flow direction of the fluid medium decreases continuously in the direction of the outlet pipe. The spacing of the top to the bottom face at the at least one delivery opening and at the fluid inlet region adjoining it in the flow direction is maximal ($b_{max}$) and preferably equivalent to from one to three times the diameter $d_z$ of the fluid inlet region ($b_{max} \leq 3\ d_z$). Preferably, the spacing of the top face to the bottom face at the at least one delivery opening and at the fluid inlet region adjoining it in the flow direction is equivalent to the single diameter $d_z$ of the fluid inlet region ($b=d_z$). With the decreasing spacing b, an imaginary intermediate plane extends through the center point of the fluid in the region parallel to the top face of the upper part of the reaction chamber.

As a result of the decreasing spacing b, a greater acceleration, based on the principle of rotary momentum, of the introduced fluid medium is advantageously achieved. Furthermore, this additional narrowing of the upper part of the reaction chamber leads to an increased viscosity of the fluid medium, $E=\dot{V}/b$. $\dot{V}$ is the volume flow and b is the spacing between the top and bottom face.

The continuity equation for the volume flow states that a volume flow in a line is always constant. This does not change even if the cross section of the line changes. This is called the Venturi effect and forms the basis for Bernoulli's Law. Based on the continuity equation $\dot{V}=c \cdot A$ (with the volume flow $\dot{V}$, the mean flow speed c and the cross sectional area A at the point being observed), the mean flow speed increases with decreasing cross-sectional area, resulting in an increase in the rotary momentum.

If the fluid inlet region is seen as a flow plane $b_0$, then the flow plane $b_1$ below or following it in longitudinal section with the radius r from the outermost point of the reaction chamber to the outer wall of the outlet pipe of this ensuing flow plane $b_1$, should be selected such that the resultant angular speed $\omega_1$ is at least 1.5 times higher than the angular speed $\omega_0$ at the fluid inlet region.

Preferably, the upper parts of the reaction chamber in plane view is a circular disk or has the shape of a plate.

According to the invention, the top and bottom faces have a setting angle of 80° to 115°, preferably from 90° to 110°, and especially preferably of 90°.

The setting angle refers to the angle which, viewed in longitudinal section in the installed state, is established relative to the longitudinal axis of the reaction chamber.

The setting angle at α=90° is established from the center plane to the longitudinal axis; the center plane extends through the center points of the fluid inlet region. This applies both to a constant spacing b between the top and bottom faces (the center plane then extends parallel to them both and to a decreasing spacing b between the top and bottom faces. The setting angle at α=90° always refers to the angle, established in the installed state, below the center plane; that is, from the center plane to the longitudinal axis of the reaction chamber. To that end, the section of the longitudinal axis with the center plane represents a Cartesian coordinate system. The setting angle α=90° thus always refers to the third and/or fourth quadrant of the Cartesian coordinate system.

The setting angle α>90° or α<90° are established from the imaginary intermediate plane to the longitudinal axis; the imaginary intermediate plane extends through the center points of the fluid inlet region and parallel to the top face of the upper part of the reaction chamber. This is applies both to a spacing b that remains constant between the top and bottom face (the imaginary intermediate plane then extends parallel to both) and to a decreasing spacing b between the top and bottom face. The setting angle α>90° or α<90° always refer to the angle, established in the installed state, below the imaginary intermediate plane, that is, from the imaginary center plane to the longitudinal axis of the reaction chamber. At a setting angle α<90°, somewhat more pressure is needed than for α>90°. At a setting angle α>90°, the introduced fluid medium has an inflow direction into the reaction chamber that drops downward in the flow direction.

At a setting angle of α=90°, the introduced fluid medium remains on one level, and only upon a transition to the lower part of the reaction chamber does a dropping motion in the flow direction ensue. The spacing b, a setting angle of α=90°, is equivalent to the height of the upper part of the reaction chamber in the installed position.

In one embodiment, the setting angle α for both halves of the reactor facility (that is, to the left and right of the longitudinal axis) in longitudinal section has the same values. Preferably, the structure] of the second half of the reactor facility on the other side of the longitudinal axis is the same, since the reactor facility is constructed mirror-symmetrically in longitudinal section. In an alternative embodiment, the values of the setting angle α on the two halves of the reactor facility in longitudinal section differ.

As a result of the rotationally symmetrical platelike or cuplike form, according to the invention, of the upper part of the reaction chamber in longitudinal section of the reactor facility, the properties and achievements of the flow dynamics treatment of fluid media, which in the reaction chamber have pronounced friction of the fluid medium up to the fluid passage, are sharply improved. The disadvantages of the fluid eddy formation in the heart-shaped reactor facility, as disclosed for example in EP 1 294 474 B2, are reduced or eliminated entirely.

The lower part of the reaction chamber is understood to be that part which in the installed state and in the flow direction of the fluid medium follows the upper part of the reaction chamber and is formed by the inner walls, on the fluid contact side, of the lower part of the housing.

The lower part of the reaction chamber has a bottom face which adjoins the bottom face of the upper part of the reaction chamber.

The bottom face of the lower part of the reaction chamber begins at the point at which the spacing b between the top and bottom face of the upper part of the reaction chamber is no longer constant or decreases but instead becomes greater. Hereinafter, this point will be described as the transition of the bottom face of the lower part of the reaction chamber. The transition of the bottom face of the lower part of the reaction chamber here includes only the bottom face coming from the upper part of the reaction chamber, but not any top face anymore, since the top face already opens into the upper part of the reaction chamber in the outer wall of the outlet pipe.

The spacing which extends from the outer wall of the outlet pipe at the beginning of the transition of the bottom face of the lower part of the reaction chamber in the flow direction is equivalent to the radius $r_3$. Here, $r_3$ can never reach or exceed the radius $r_1$ or the maximum radius $r_{max}$ of the upper part of the reaction chamber.

In a preferred embodiment, $r_1$ is at least twice as large as the diameter $d_z$ of the fluid inlet region ($r_1 \geq \frac{1}{2}\ d_z$). In a very particularly preferred embodiment, $r_1$ is at least greater than the sum of the diameter $d_z$ of the fluid inlet region and the spacing $r_3$ from the transition of the bottom face of the lower part of the reaction chamber to the outer wall of the outlet pipe ($r_1 \geq d_z + r_3$).

In one embodiment, the transition of the bottom face of the lower part of the reaction chamber assumes an arbitrary contour. In a preferred embodiment, the transition of the bottom face of the lower part of the reaction chamber assumes a curvature. In a further embodiment, the transition of the bottom face of the lower part of the reaction chamber deviates abruptly away from the bottom face of the upper part of the reaction chamber toward the longitudinal axis.

In one embodiment, the lower part of the reaction chamber in the flow direction of the fluid medium has a spacing from the outer wall of the outlet pipe that decreases from a transition of the bottom face of the lower part of the reaction chamber to the floor region of the lower part of the reaction chamber.

Preferably, the decreasing spacing is continuous. Advantageously, the fluid medium is as a result accelerated faster, and fewer pressure losses occur in the reaction chamber.

In an alternative embodiment, the lower part of the reaction chamber in the flow direction of the fluid medium has a spacing that decreases abruptly from the transition of the bottom face to the floor region toward the outer wall of the outlet pipe.

The lower part of the reaction chamber extends in the flow direction of the fluid medium from the transition of the bottom face of the lower part of the reaction chamber to a lower boundary of the floor region.

The floor region of the lower part of the reaction chamber forms the lower boundary, in the installed state, of the lower part of the reaction chamber and continues as a wall from the transition of the bottom face of the lower part of the reaction chamber onward.

In one embodiment, the floor region in the flow direction of the fluid medium begins at a curvature of the transition of the bottom face of the lower part of the reaction chamber.

In one embodiment, the wall of the floor region of the lower part of the reaction chamber assumes an arbitrary contour. Preferably, the floor region is curved. Especially preferably, the floor region is curved in concave fashion. The term "concave curvature" is understood here to mean a bulge projecting in longitudinal section outward, that is, downward in the installed state. In an alternative embodiment, the floor region is designed as a paraboloid. In a further alternative embodiment, the floor region has a different contour, such as an angular contour.

As a result of the preferred curved floor region, the course of the walls of the lower part of the reaction chamber is reversed, and the fluid medium is diverted in its flow direction. Advantageously, the majority of the components to be treated in the fluid medium, such as organic components, are made to burst open because of the diversion of the fluid eddy.

The curved floor region of the lower part of the reaction chamber in the installed state includes a lower boundary, which extends along the lower region of the lower part of the reaction chamber.

The spacing in which the lower part of the reaction chamber extends from the transition of the bottom face of the lower part of the reaction chamber to the lower boundary of the curved floor region is called the spacing z. In other words, the spacing is defined from that point at which the spacing b between the top and bottom face of the upper part of the reaction chamber is no longer constant or decreases, but instead becomes greater.

In one embodiment, the spacing z is variable. In a preferred embodiment, the spacing z amounts to at least half the diameter $d_z$ of the fluid inlet region ($z \geq \frac{1}{2} d_z$), in order advantageously to generate friction inside the fluid eddy.

In one embodiment, in the lower boundary of the floor region of the lower part of the reaction chamber, a geometrically ascending fluid passage is inserted, the longitudinal axis of which coincides with the longitudinal axis of the rotationally symmetrical reaction chamber. In the case of an inserted fluid passage, the contour of the lower part of the reaction chamber extends from the lower boundary of the floor region continuously to the fluid passage, or its eversion.

The at least one delivery opening is located in the upper part of the reaction chamber. Because of the at least one delivery opening, the media inflow thus takes place into the upper part of the reaction chamber.

Preferably, the housing has at least one opening for an inlet pipe, as a result of which the fluid medium in at least one inlet pipe is conducted through the at least one delivery opening, formed and located tangentially to the cross section of the jacket face, into the upper part of the reaction chamber. Advantageously, as a result of only a single delivery opening, less energy is expended for the medium flow into the reaction chamber.

In a preferred embodiment, the fluid medium is introduced through more than one delivery opening, located tangentially to the jacket face of the upper part of the reaction chamber, into the upper part of the reaction chamber, for instance through two, three, four or more delivery openings. In a further preferred embodiment, the upper part of the reaction chamber has two delivery openings, which are located horizontally opposite one another in the upper part of the reaction chamber.

The fluid medium to be treated is introduced from an inlet pipe, located outside the reactor facility, through the opening in the housing and the adjoining at least one delivery opening formed there, into the upper part of the rotationally symmetrical reaction chamber. The inlet pipe for the media inflow is equivalent to the main inflow, or to pipelines branching off from it.

The inlet pipe leads through the opening in the housing and intersects the jacket face of the upper part of the reaction chamber tangentially in cross section, as a result of which an obliquely cut-off circular cylinder, and thus the at least one delivery opening, are formed. The fluid medium to be treated thus enters tangentially to the cross section of the jacket face of the upper part of the reaction chamber through the at least one delivery opening into the upper part of the reaction chamber.

In one embodiment, the inlet pipe represents a pipe inflow line and thus an elongated hollow body, preferably a round pipe with a circular face in cross section. The at least one delivery opening, because of the intersection of the inlet pipe with the jacket face of the upper part of the reaction chamber, has a circular or elliptical face.

The at least one delivery opening is adjoined in the flow direction in the upper part of the reaction chamber by a fluid inlet region, which receives the fluid medium, flowing into the reaction chamber through the at least one delivery opening, and carries it onward. The fluid inlet region has a diameter $d_z$. In a preferred embodiment, the at least one delivery opening and the fluid inlet region adjoining it in the flow direction are located in the transition region from the top to the bottom face. In a very particularly preferred embodiment, the center point of the fluid inlet region is located along the center plane.

In one embodiment, precisely one fluid medium is conducted through a delivery opening into the adjoining fluid inlet region of the upper part of the reaction chamber. In an alternative embodiment, more than one fluid medium is conducted into the reaction chamber, preferably in each case through a delivery opening. Alternatively, more than one fluid medium is conducted through the same delivery opening into the reaction chamber. The fluid media can be identical or different. The fluid media can originate in the main inflow or in pipelines branching off from it or in other inflow pipes.

The outlet pipe is a pipe embodied as a continuous hollow cylinder and it is introduced in sealing fashion into an opening located centrally in the upper part of the housing in the longitudinal section of the reactor facility along the longitudinal axis.

In a special embodiment, the outlet pipe consists of a plurality of cylindrical hollow parts. In the invention, the outlet pipe is divided into an upper part and a lower part.

In one embodiment, the outlet pipe is displaceable relative to the centrally located opening in the housing and thus relative to the reaction chamber along the longitudinal axis and is adjustable and thus advantageously adapts to the properties and treatment of the fluid medium. The adjustment of the outlet pipe is effected via a mechanical adjusting unit. The outlet pipe is received in such a way, in an axial bearing, connected firmly to the housing or fixed relative to it, that an adjustment along the longitudinal axis is also possible during operation, without a change in the position of the intersection between the housing and the pipeline of the main inflow or other inflow lines. As a result, an adaptation of the operating parameters can be done at any time as needed and without major effort.

The outlet pipe in its longitudinal axis coincides with the longitudinal axis of the rotationally symmetrical reaction chamber. The outlet pipe, measured from the longitudinal axis to the outer wall of the outlet pipe, has a radius $r_2$. In one embodiment, the spacing $r_2$ is constant at all points of the outlet pipe. In an alternative embodiment, the spacing $r_2$ is not constant at various points of the outlet pipe. This is due to a varying spacing from the outer wall to the inner wall of the outlet pipe, which is designated as the wall thickness d.

In one embodiment, the inner walls of the outlet pipe are in contact with the fluid medium and thus are fluid-carrying.

What in the installed state is the upper part of the outlet pipe is located in the upper part of the reaction chamber, or in other words outside the housing. The outlet pipe in the upper part has an upper region, near the mouth, that protrudes from the housing and can be embodied as an inspection pipe. The end of the upper region near the mouth is embodied as an outlet opening for the fluid medium and is located outside the housing. Here, the exit of the fluid medium (media exit) takes place from the reactor facility.

The total cross section of the outlet opening is composed of the free cross section and the wall thickness of the outlet pipe: $d_{ges}=2 \cdot r_2=2 \cdot (d+d_{frei})$. The free cross section $d_{frei}$ of the outlet opening, through which the diverted fluid medium leaves the outlet pipe, represents the spacing between the two inner walls, opposite one another and in contact with the fluid, of the outlet pipe at the end of the upper region, near the mouth, and is calculated from the difference between the total cross section of the outlet opening and the wall thicknesses: $d_{frei}=d_{ges}-(2 \cdot d)=(2 \cdot r_2)-(2 \cdot d)$.

What in the installed state is the lower part of the outlet pipe is located for the most part in the lower part of the reaction chamber, or in the floor region of the lower part of the reaction chamber. The outlet pipe in the lower part has a lower region near the mouth, which region in the flow direction of the fluid medium adjoins the inlet opening of the outlet pipe. The region near the mouth of the lower part of the outlet pipe extends along its longitudinal axis to almost the lower boundary of the floor region of the lower part of the reaction chamber. The end of the lower region near the mouth is embodied as an inlet opening, which is located in level fashion and is perpendicular to the longitudinal axis, for the fluid medium diverted at the floor region.

The total cross section of the inlet opening is composed of the free cross section and the wall thickness of the outlet pipe: $d_{ges}=2 \cdot r_2=2 \cdot (d+d_{frei})$. The free cross section $d_{frei}$ of the inlet opening, through which the diverted fluid medium reaches the outlet pipe, represents the spacing between the two inner walls, opposite one another and in contact with fluid, of the outlet pipe at the end of the lower region near the mouth and is calculated from the difference between the total cross section of the inlet opening and the wall thicknesses: $d_{frei}=d_{ges}-(2 \cdot d)=(2 \cdot r_2)-(2 \cdot d)$. Preferably, the inlet opening and the outlet opening have the same value for the free cross section $d_{frei}$. Also preferably, the free cross section $d_{frei}$ decreases only in the vicinity of the nozzle for attaining the Venturi effect.

The inlet opening of the outlet pipe, according to the invention, is located at a spacing a from what in the flow direction is the lower boundary of the curved floor region of the lower part of the reaction chamber. In one embodiment, the inlet opening is located at a variable spacing a from the lower boundary of the curved floor region. In a further embodiment, the inlet opening is located at a slight spacing a from the lower boundary of the curved floor region. Preferably, the spacing a between the inlet opening of the outlet pipe and what in the flow direction is the lower boundary of the curved floor region is less than the diameter $d_z$ of the fluid inlet region ($a<d_z$).

In one embodiment, the spacing a between the inlet opening and the lowermost boundary of what in the flow direction is the lower part of the reaction chamber is equal to small than the total cross section $d_{ges}$ of the inlet opening.

The inlet opening of the outlet pipe is adjoined in the flow direction of the fluid medium by the lower region, near the mouth, of the outlet pipe. In one embodiment, the outlet pipe in this region is designed in the interior as a hollow pipe, with a constant spacing between the two inner walls, facing one another, that are in contact with the fluid. Preferably, the constant spacing is equivalent to the free cross section $d_{frei}$. Especially preferably, the inlet opening, the outlet opening, and the region between them (that is, between the lower and upper regions near the mouth) has the same value for the free cross section $d_{frei}$.

In a preferred embodiment, the region, near the mouth, of the outlet pipe is embodied as a nozzle for attaining the Venturi effect, hereinafter also simply called nozzle. For attaining the Venturi effect, the inner walls of the outlet pipe which are in contact with the fluid each have a narrowest point; these points form the nozzle. This is as a rule the point having the smallest free cross section of the inner walls, in contact with the fluid, of the outlet pipe. That in turn leads to an increase in the wall thickness d of the outlet pipe.

If the total cross fluid cross section $d_{ges}$ of the inlet opening of the outlet pipe is smaller than the diameter of the fluid inlet region ($d_{ges}<d_z$), then based on Bernoulli's equation, the pressure at the inlet opening of the outlet pipe drops. If the lower region, near the mouth, of the outlet pipe is embodied as a nozzle with the smallest free cross section, then the pressure is established such that in the nozzle for attaining the Venturi effect, a negative pressure ensues.

Advantageously, the nozzle for attaining the Venturi effect can be exchanged or replaced in the event of cleaning, damage, or defects. In a preferred embodiment, the nozzle is designed as a Venturi nozzle. In a further preferred embodiment, the nozzle is designed as Laval nozzle.

The fluid passage consists of a single (massive) body. In an alternative embodiment, the fluid passage consists of a plurality of components. If in what follows the term fluid passage is used, this always refers to what in the installed state is an upper part of the entire fluid passage component, which is introduced into the lower part of the reaction chamber.

In one embodiment, the fluid passage is introduced through a centrally located opening in what in the installed state is the lower part of the housing in sealing fashion into the lower boundary of the floor region of the lower part of the reaction chamber. In an alternative embodiment, the fluid passage is a part of the housing and thus is already fixedly integrated with the lowermost part thereof. In one embodiment, the longitudinal axis of the fluid passage coincides with the longitudinal axis of the rotationally symmetrical reaction chamber.

The fluid passage precedes the outlet pipe in the flow direction of the fluid medium. In one embodiment, the fluid passage is shaped geometrically and mirror-symmetrically to the longitudinal axis of the reaction chamber.

In one embodiment, the fluid passage is shaped geometrically flatly relative to the longitudinal axis of the reaction chamber.

In a preferred embodiment, the fluid passage is shaped in ascending fashion geometrically to the longitudinal axis of the reaction chamber, preferably in elongated fashion, and has a tubular spigot, hereinafter called the eversion of the fluid passage, or eversion for short.

The length of the eversion can be designed variably. Preferably, the eversion protrudes into the floor region of the lower part of the reaction chamber. The inlet opening of the outlet pipe is located centrally on the longitudinal axis of the reaction chamber to the eversion of the fluid passage. In one embodiment, the eversion projects as far as the inlet opening of the outlet pipe.

In an especially preferred embodiment, the length of the eversion is advantageously designed such that it ends in the narrowest part of the nozzle, namely at the location in the nozzle that has the smallest free cross section of the inner wall, in contact with the fluid, of the outlet pipe and that is thus the nozzle for attaining the Venturi effect. Advantageously, the flow dynamics treatment of the fluid medium is optimized by this position.

In a preferred embodiment, the fluid passage is displaceable and adjustable relative to the floor region of the housing and thus relative to the floor region of the reaction chamber along the longitudinal axis and thus advantageously adapts to the properties and treatment of the fluid medium.

Furthermore, the spacing between the fluid passage and the inlet opening of the outlet pipe is variably adjustable centrally along the longitudinal axis, so that the fluid passage, if there is a change in position of the outlet pipe, can advantageously be made to track along the longitudinal axis. Since the outlet pipe is also variably adjustable along the longitudinal axis, it is conversely possible for the outlet pipe, upon a change in position of the fluid passage, to be readjusted along the longitudinal axis.

The fluid passage is preferably adjustable and displaceable in the same way as the outlet pipe relative to its opening in the housing along the longitudinal axis of the reaction chamber, as a result of which the pressure and flow conditions in the reaction chamber can advantageously be optimized. To that end, the adjustment mechanism of the fluid passage is designed such that its readjustment or reregulation in an optimal negative pressure region for the diversion of the fluid eddy, generated by the reactor facility of the invention, into the outlet pipe is made possible.

According to the invention, by a change in direction, the fluid eddy at the fluid passage is diverted into the inlet opening of the outlet pipe by means of a ascending motion that is counter to what, in the installed state, is a downward-oriented translational and rotary motion along the longitudinal axis.

At a setting angle of $\alpha=90°$, the fluid medium in the upper part of the reaction chamber is set into rotation and rotates along the center plane to the outlet pipe. The angular momentum of the fluid medium remains constant over the entire range of the upper part of the reaction chamber and advantageously decreases only at the transition of the fluid medium into the lower part of the reaction chamber as a result of the descending motion, in terms of the flow direction, of the fluid medium.

The function of the reactor facility of the invention is based on the initiation of physical, mechanical and chemical reactions by creating suitable pressure conditions in the reaction chamber.

The intensity and thus the effectiveness of the reactor facility of the invention are dependent on pressure, speed and temperature. The rotationally symmetrical design of the reaction chamber brings about such a major acceleration of the volume flow in the developing fluid eddy that the biological, physical and chemical processes taking place in the fluid medium are sped up. The volume flow is established variably, among other reasons as a function of the size of the reaction chamber or in other words the reaction chamber volume.

Because of the shape of the fluid-carrying rotationally symmetrical reaction chamber, translational and rotary motions of the at least one introduced volume flow of the fluid medium, which develops a fluid eddy, occur along the longitudinal axis. The fluid eddy in the process is guided in the flow direction in the installed state toward the lower end of the reaction chamber, around the outlet pipe, and (in the case where $\alpha>90°$) takes on the motion of a descending helical line that is oriented downward in the flow direction. The result is the formation of a fluid eddy, which is guided in rotating fashion into the lower part of the reaction chamber and undergoes an acceleration. The acceleration is dependent primarily on the parameters $r_1$, b, $r_3$, z and $\alpha$.

As a result of the tapering of the lower part of the reaction chamber in the longitudinal axis of the reactor facility in the flow direction of the fluid medium, the fluid eddy is accelerated sharply. The kinetic energy of the elementary particles in the fluid eddy ascends because of the tapering of the lower part of the reaction chamber and leads to an increase in the reactivity of the fluid medium.

Advantageously, the translational and rotary motions are superimposed on one another. The inflow speed of the at least one fluid medium should be selected such that in flow terms a turbulent boundary layer can develop; the at least one fluid eddy generated is accelerated; and a high speed difference ensues.

Advantageously, a combination of translational motion and simultaneous rotary motion is selected such that in the event that there are a plurality of volume flows, they touch one another.

The structural design of the invention is selected such that upon flowing through the reaction chamber at a defined dynamic pressure, a speed with as high as possible a maximum value and as large as possible a gradient in the radial direction is imparted.

The flow conditions, required for producing as strong as possible an advantageous friction and centrifugal action and as great as possible shear stresses in the fluid eddy to be treated, are achieved by means of the structural design of the reactor facility. By the form of the reaction chamber, the fluid eddy of the fluid medium to be treated is steered in such a way that in the descending branch of the flow course, that is, between the at least one delivery opening with an ensuing fluid inlet region and the inlet opening of the outlet pipe, a fluid eddy is embodied. The flow speed of the fluid eddy has a pronounced gradient over its cross section in the radial direction.

By the tapering of the lower part of the reaction chamber in longitudinal section of the reactor facility in the flow direction of the fluid medium and by the location of the at least one delivery opening and the inlet opening of the outlet pipe, on the one hand shear stresses between the individual flow layers of the fluid eddy are produced. Such shear stresses are also produced between the walls of the reaction chamber, the outer wall of the outlet pipe secured in the reaction chamber, and the fluid eddy. The frictional forces, produced by the shear stresses and opposite to them, of the fluid eddy lead, because of a new arrangement of the bonds between the molecules of the fluid medium to be treated, to a change in the surface tension and a change in the viscosity of the fluid medium.

Advantageously, a separation of substances can be achieved because of the different specific weights of the substances found in the fluid medium, and is intensified by the superposition of the translational and rotary motion.

A grinding action is attained as well. The physically produced high speed difference between the individual layers of the fluid eddy lead to a mechanical disintegration of solid organic components, such as bacteria, algae and other microorganisms as well as inorganic components. The resultant debris is as a consequence broken down mechanically and chemically. This mechanical breakdown of the organic and inorganic components takes place to a slight extent because of the geometry of the reaction chamber, even before the fluid eddy formed is diverted at the fluid passage.

Between the upper and lower parts of the reaction chamber, pressure differences occur, which advantageously contribute to producing a fluid eddy. The resultant pressures in the reaction chamber are dependent, among other things, on the design and form of the reaction chamber or the shape of the nozzle. In the floor region upstream of the inlet opening of the outlet pipe, a pilot pressure, which is preferably at >ca. 3-4 bar, a dynamic pressure increasing in the flow direction, and a resultant negative pressure or vacuum all prevail.

Because of the advantageous shape of the upper part of the reaction chamber, in comparison to EP 1 294 474 B2, less pressure and thus less energy is needed in order to put the fluid medium, flowing in through the at least one delivery opening, into rotation. On the other hand, because of the advantageous shape of the upper part of the reaction chamber, at the same required pressure and energy in comparison with EP 1 294 474 B2, a higher rpm speed and rotary speed of the fluid eddy are achieved.

The walls of the reaction chamber are machined in such a way that they have a lower coefficient of friction than before the machining and thus the fluid medium can be advantageously accelerated in the reaction chamber. The coefficient of friction is dependent on the corresponding material suitably used for the reaction chamber.

As a result of the design of the reactor facility of the invention, the fluid medium in the upper part of the rotationally symmetrical reaction chamber, on the basis of the principle of angular momentum, is guided in the form of a guided fluid eddy along the longitudinal axis in the flow direction into the lower part of the reaction chamber. It is advantageous here, and in comparison to EP 1 294 474 B2, only slight losses of flow energy occur. The angular momentum of the fluid medium varies only slightly.

In the lower part of the reaction chamber, the rotating fluid eddy is diverted toward the center of the flow at the fluid passage and is diverted there in an opposite ascending direction along the longitudinal axis of the reaction chamber, preferably into the nozzle of the outlet pipe. Preferably, at the fluid passage the rotating fluid eddy arriving from above is diverted oppositely to its original direction. In that process the fluid eddy abuts against the fluid passage, and an eddy indentation occurs. Very particularly preferably, the fluid eddy abuts against the eversion of the fluid passage.

The centrifugal and centripetal forces and the frictional forces caused by shear stresses between flow layers moving at different speeds act variously strongly in the floor region of the lower part of the reaction chamber as well as on the variously heavy components contained in the fluid medium.

In the floor region, there is a strong centrifugal effect, because the inorganic and/or organic contaminants entrained as floating particles are driven, because of their high weight, from the center of the fluid eddy to its edge. The dissolved gaseous components, because of their low weight, are driven from the edge of the fluid eddy toward its center.

In the change of direction of the fluid eddy that takes place, because of the diversion in the floor region, the already-separated contaminants and media of different weights move again in the opposite direction, via the cross section of the fluid eddy.

Thus in the lower region of the reaction chamber, in the vicinity upstream of the inlet opening of the outlet pipe, at least two volume flows operate counter to one another (the volume flow of the fluid eddy arriving from above in the installed state and the volume flow of the diverted fluid eddy). Upstream of the inlet opening of the outlet pipe, a lower pressure develops than in the rest of the reaction chamber.

As a result of the developing pressure conditions in the floor region of the reaction chamber as well as upstream of the inlet opening of the outlet pipe, the cell walls of the organic components contained in the fluid medium are made to burst open. Moreover, collision and friction of the impurities dissolved in the fluid medium cause the mechanical and physical destruction and comminution of these impurities. The impurities dissolved in the fluid medium include organic and/or inorganic substances, substance compounds, microorganisms, and botanical and/or organic living things, such as germs, bacteria, fungi or algae among one another, as well as the individual particles, atoms and atomic groups, and molecules of the fluid medium.

The high kinetic energy, the energy input from friction of the individual layers in the at least one fluid eddy, and the attendant centrifugal force and/or translational force result in an optimal energetically stable and balanced status and bond thus effect a change in the normally present surface tension and viscosity. This rearrangement of the grid structure is due to the breaking up and re-formation of the existing covalent bonds resulting from their different atom masses and thus different mass inertia as well as to collisions of the individual particles, atoms and atom groups as well as molecules with one another.

The fluid medium treated according to the invention maintains its surface-tensed status over a relatively long period of time.

By the thus-attained rearrangement of the molecular structure, dissolved gases or volatile impurities dissolved in the fluid medium are released, so that degassing of the fluid medium occurs in addition. As a result of this degassing, additionally unwanted reactions of these entrained substances in the fluid medium itself to be treated, other entrained substances, or substances which come into contact with the fluid medium, such as measurement sensors or pipe walls, are reduced or prevented.

The centrifugal force and/or translational force should be selected such that breaking up of the substance bonds and molecular chains of the impurities dissolved in the fluid medium occurs, and these are mechanically destroyed or comminuted and/or the existing impurities or the atoms, molecules or molecular compounds of the fluid medium are at least partially ionized or radicalized.

By the geometric design of the rotationally symmetrical reaction chamber, the requisite high speeds that are strongly affected by a gradient are generated in the fluid medium. These speeds are needed to produce the physical effects, that is, to disintegrate decontsolid components and to rearrange molecular bonds, and for tripping and accelerating the chemical processes by the delivery of energy. The quantity and quality of the mechanical destruction and comminution can be adjusted by varying the speeds, depending on the fluid medium on hand and on the impurities dissolved in it. The quantity and quality are dependent on the resistance of the impurities to mechanical stresses.

Entrained substances are dissolved out of the grid structure of the fluid medium and/or separated from the fluid medium via the centrifugal force because of the different specific substance weights and can after that, on being carried out of the reaction chamber, be filtered out, sedimented or otherwise bound through the outlet pipe. By the comminution of substances, the electrical conductivity of the fluid medium can be increased.

By the design of the outlet pipe in the lower region, near the mouth, as a nozzle for attaining the Venturi effect in combination with the fluid medium delivered to the reaction chamber, the fluid eddy, which develops as a hollow eddy, in the outlet pipe is highly accelerated and has low surface tension. As a result, in liquid fluid media the vapor pressure in the core region can be reached or undershot. The result is a flow with highly different speeds in the core region and the peripheral region.

A hollow eddy is formed, in the center of which a core of a fluid medium that is lighter than in the rest of the flow field forms. At increasing speeds, eddy flows with eddy filaments or eddy tubes are produced, or, depending on the type of fluid medium, a rotation-free fluid eddy with an eddy core, also known as a potential eddy, is produced. In this process, once again shear stresses in the flowing fluid medium are achieved, which further promote the physical and chemical processes.

This hollow eddy with an eddy core, which forms a vacuum, is superimposed on the vacuum development occurring in the nozzle with a Venturi effect because of the Venturi effect.

By means of the superimposed and intensified vacuum formation in the nozzle region, germs and bacteria that have an internal cellular pressure (turgor) are torn up and oxidized. In the vacuum region, dissolved gases in a liquid fluid medium are dissolved and degassed because of the existing fluid eddy.

If in counterflow via the fluid passage, which in the center along the longitudinal axis can have a through bore of adjustable flow, a gas can be delivered to the reaction chamber as an additional fluid and thus mixes with the fluid eddy and is dissolved markedly better in the fluid medium because of the altered molecular structure of the fluid medium.

The device of the invention and the method of the invention are especially advantageous because an effective, economical process can be performed at low cost in terms of both space and funds, without adding environmentally harmful chemicals and without irradiating the fluid medium or taking other potentially dangerous actions. In the course of this process, depending on the intended use, liquid waste can be decontaminated and disinfected and used again, and water reservoirs are kept germ-free. In regions with a shortage of water, a supply of fresh water can be ensured; the wetting power of various liquids can be increased. The use of detergent chemicals for various cleaning purposes in the household and industry can be significantly lessened, and the environmental strain can be reduced. Thick liquid media can be diluted purely mechanically, without a chemical change.

As a result of the design according to the invention of the reactor facility and the upper part of the reaction chamber, the fluid eddy attains an elevated rotary speed, as a result of which the efficiency of the destruction and comminution of the impurities is considerably and advantageously enhanced. By the design according to the invention of the reaction chamber, and especially the upper part of the reaction chamber, the vapor diffusion pressure is not reached until the change in direction of the fluid eddy is produced as a result of diversion at the fluid passage along the longitudinal axis by means of the rotary speed. As a result, an energy saving by means of a pressure reduction of up to 50%, preferably 20-40%, and very particularly preferably 20-30% is advantageously possible.

It should be noted that the fluid media delivered to the reaction chamber differ in terms of their properties, such as their surface tension or viscosity, and thus engender other chemical reactions and measurement parameters in the reactor facility of the invention. The measurement parameters thus vary depending on the fluid media employed.

Advantageously, a catalyst can be added to speed up the chemical reactions in the reactor facility. In a particular embodiment, at least a portion of the fluid-carrying walls of the reaction chamber is catalytically coated, or the fluid-carrying walls of the reaction chamber consist entirely of a catalytic material.

Furthermore, the chemical reactions can be speeded up by raising the temperature of the fluid media in accordance with the thermal state equation of ideal gases. Advantageously, the reaction speed is higher because of the higher energy input resulting from a temperature increase. For that purpose, already-warmed fluid media such as warm or hot liquid waste can be delivered to the reactor facility and treated using flow dynamics. In an alternative embodiment, the reactor facility is connected to a heater, such as a heating plate, and associated heat control for heating up the fluid media.

Furthermore, peripheral components such as hoses or pipes for transporting the fluid medium, pressure valves such as overpressure valves, flow adjusters, and pretreatment units can be attached to the reactor facility of the invention. The use of pumps and/or compressors in conjunction with the adjustability of the outlet pipe and of the free cross section of the inlet opening of the outlet pipe generates the requisite dynamic pressure.

In one embodiment, a device for measuring pH value is connected to the reactor facility. In one embodiment, the reactor facility is used in an open pipeline system. Thus the pH value of the fluid medium can advantageously be measured after the flow dynamics treatment.

Furthermore, the gases that occur during the flow dynamics treatment of the fluid medium are carried away with the fluid medium out of the outlet opening of the outlet pipe and out of the reactor facility as a result of the rotary motion and neutralized.

In an alternative embodiment, the reactor facility is used in a closed circulation system. The gases occurring during the flow dynamics treatment are carried away from the outlet opening of the outlet pipe with the fluid medium by rotary motion and neutralized. In one embodiment, the carried-away gases that occur are collected in a device for intercepting them separately. Preferably, these are special containers for intercepting gases. Advantageously, a hydrogen-oxygen reaction is averted by the separate interception as well as an ensuing neutralization.

In a special embodiment, the interception gases are used again and for example are advantageously used for fuels or heating materials such as methane, methanol, or benzene.

In a preferred embodiment, the fluid passage has at least one through bore along the longitudinal axis, and the longitudinal axis of the through bore coincides with the longitudinal axis of the rotationally symmetrical reaction chamber.

Through the through bore along the longitudinal axis of the fluid passage, the reaction chamber can advantageously be preferably supplied with at least one additional fluid medium, which is aspirated as needed directly and automatically into the lower part of the reaction chamber by means of the negative pressure prevailing in the floor region of the reaction chamber. Advantageously, the fluid eddy is thus diverted at the fluid passage and can also be mixed with an additional fluid medium.

In one embodiment, the fluid passage is shaped as geometrically flat relative to the longitudinal axis of the reaction chamber and has a through bore. In a preferred embodiment, the fluid passage is shaped as ascending geometrically, preferably longitudinally, relative to the longitudinal axis of the reaction chamber and has a tubular spigot, hereinafter called the eversion of the fluid passage, or eversion for short, which has a through bore.

If the length of the eversion of the fluid passage is shaped such that it ends directly in the nozzle for attaining the Venturi effect, the fluid medium additionally aspirated through the through bore is thus aspirated directly into the interior of what in the installed state is the lower region, near the mouth, of the outlet pipe.

In the elongated embodiment of the fluid passage with the through bore along the longitudinal axis, the intended delivery or aspiration of an additional fluid medium directly through the inlet opening of the outlet pipe, into its lower region near the mouth, is advantageous. Preferably, the lower region of the outlet pipe near the mouth is embodied as a nozzle for attaining the Venturi effect, as a result of which the additional fluid medium is aspirated directly into the nozzle for attaining the Venturi effect.

The length of the eversion can be designed in variable ways. In a particularly preferred embodiment, and for the highest efficiency of the reactions, the length of the eversion is advantageously designed such that it ends in the narrowest part of the nozzle, that is, the place in the nozzle having the smallest free cross section of the inner walls, in contact with fluid, of the outlet pipe. The flow dynamics treatment of the fluid medium is advantageously optimized in this position.

The addition of media for chemical secondary reactions in the outlet pipe is done by pressure or advantageously by using the negative pressure in the nozzle for attaining the Venturi effect.

In one embodiment, an additional fluid medium is delivered to the reaction chamber. That medium can be aspirated through the through bore of the fluid passage, or it can reach the adjoining fluid inlet region of the upper part of the reaction chamber via the main inflow or other supply lines via the at least one delivery opening.

In one embodiment, a plurality of additional fluid media are delivered to the reaction chamber. These media can all be aspirated through the through bore of the fluid passage, or they can reach the reaction chamber via the main inflow or other supply lines via the at least one delivery opening. In a further embodiment, the fluid media reach the reaction chamber through the fluid passage as well as via the main flow or other supply lines via the at least one delivery opening. Also, solid materials dissolved in the additional fluid medium can be aspirated into the reaction chamber through the through bore and/or the at least one delivery opening.

In one embodiment, the at least one additional fluid medium can be the same medium that is delivered to the reactor facility through the at least one delivery opening in the upper part of the reaction chamber. In alternative embodiment, the at least one additional fluid medium is some other fluid medium than the one which is delivered to the reactor facility through the at least one delivery opening in the upper part of the reaction chamber. As a result, a targeted dosage of further additional fluid media is possible.

By means of the additionally delivered fluid media, chemical or biological reactions can be preferentially improved or accelerated, in that substances affecting chemical or biological reactions, such as oxidation or precipitation agents, are made to react. As additional delivered fluid media, oxidants such as ozone, hydrogen peroxide, or oxygen or other additional fluid media serving as reaction partners and*catalysts, which are delivered to the reaction chamber from a reservoir, can be considered.

If the additional delivered fluid medium is gaseous and an oxidant, such as oxygen or from oxygen from the (ambient) air, then it can be ionized by a preceding pretreatment device or converted into radicals such as ozone, to improve the oxidation properties. As a result, hydrocarbon compounds and/or other organic compounds, such as germs, bacteria and extremely small organisms, can be oxidized. The result among other things is water and carbon dioxide; that is, with organic substances, denaturing takes place.

A significant increase in the reaction speed is brought about by the dosed feeding in of oxidants or other additional fluid media serving as reaction partners.

The most important areas of use of the method of the invention and of the fluid media treated by the device of the invention are industry, commerce, private households, foodstuff production, land and forest management, the waste and disposal industry, cleaning technology, sterilization, canning, mechanical engineering, electronics, medicine and therapy, the construction industry, and energy technology. The device and the method of the invention are preferentially used for pretreatment, processing, sterilization, disinfection and/or the initiation of mechanical, physical and chemical reactions of and in fluid media. Preferably, this involves aqueous fluid media.

According to the invention, the terms pretreatment, processing, sterilization, disinfection and/or initiation of mechanical, physical and chemical reactions are understood to mean the cleaning and cleansing of fluid media, in which the proportion of harmful substances is reduced. Harmful substances are organic or inorganic components or microorganisms, which can also be poisonous, dissolved in the fluid medium.

For instance, hydrocarbons, germs, fungi, algae and bacteria found in aqueous solutions are destroyed by causing organic components to burst, and in the process poorly soluble and toxic inorganic components are destroyed. Especially preferably, drinking water, process, liquid waste or grey water are pretreated, processed and/or disinfected. Long-chain molecular compounds can also be comminuted.

For example, the water in swimming pools is disinfected thereby. Advantageously, the device of the invention and the method of the invention can be employed in the autonomous supply of drinking water, but also in (mobile) processing of liquid waste in mobile homes and in processing liquid waste in isolated mountain villages or autonomous vacation camps.

The device and method of the invention are preferably employed to treat liquid wastes, especially private, industrial or community sewage. For instance, hydrocarbon compounds dissolved therein are at minimum cracked open and then consumed by other bacteria. Furthermore, bodies of water can be cleaned with the device and method of the invention. Industrially produced soapy water is also cleaned this way.

Liquid wastes containing minerals, such as those that occur for instance at service stations (car) washing systems, industrial washing systems, and highly polluted organically, such as in biogas systems, are advantageously cleaned using the device and method of the invention. Tensides that occur in liquid wastes can also be cleaned and processed.

Furthermore, with the device and method of the invention, lubricating oil emulsions as well as heavy oils can also be cleaned.

If parts of an auto body are shaped, the pieces of metal painted with grease have to be cleaned again with hot water before being painted. The cleaning water must likewise be cleansed of greases and tensides. This processing of the residue water, which occurs in shaping metal bodies after metal washing, can likewise be accomplished by the device and method of the invention.

Furthermore, gaseous or liquid fuels, which are preferentially based on vegetable oils, can also be treated.

The device and method of the invention have particular advantages, in that at little expense in terms of space and cost, an effective, economical process can be performed without adding environmentally harmful chemicals and without irradiating the fluid medium or taking other potentially dangerous provisions. As a result, depending on the intended use, liquid waste can be decontaminated and disinfected and used again; water reservoirs can be kept germ-free. In areas where water is scarce, a supply of fresh water can be ensured. The usability of various liquids can be enhanced. The use of detergent chemicals can be significantly reduced for various cleaning purposes in the household and industry and thus the environmental strain is reduced. Thick liquid media without chemical alteration can be diluted in purely mechanical ways.

EXEMPLARY EMBODIMENTS

The invention will be described below in further details by means of exemplary embodiments. The exemplary embodiments are intended to describe the invention without restricting its scope.

The invention will be described in further detail with the aid of drawings. In the drawings.

Figure 1:
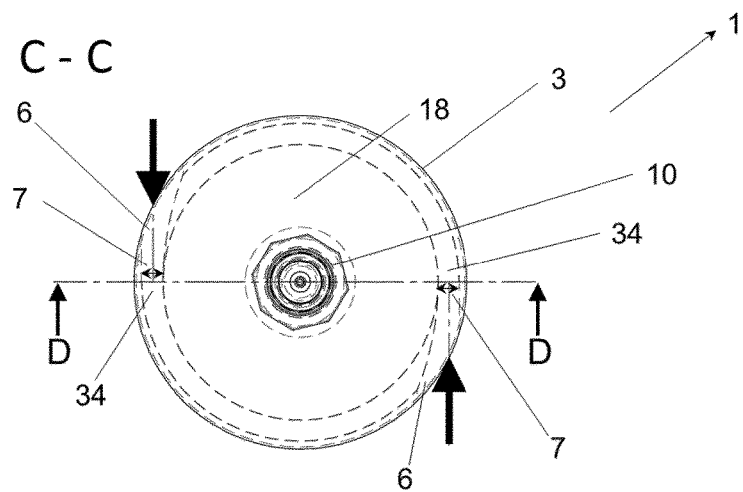
FIG. 1 is a plan view, in cross section along the sectional plane C-C, onto the reactor facility of the invention.

FIG. 1 in plan view and in cross section along the plane C-C shows the reactor facility 1 of the invention with the upper part of the housing 3 and the outlet pipe 10. Two inlet pipes (not shown) that in longitudinal section of the reactor facility 1 are opposite one another along the plane D-D discharge, in the view along the plane C-C, tangentially to the jacket face of the upper part of the reaction chamber 18 and form two delivery openings 6, which in section have an elliptical surface with the jacket face. The two arrows before the respective delivery openings 6 represent the flow direction of the fluid medium. The delivery openings 6 are each adjoined by the fluid inlet regions 34 in the flow direction, and these regions, in longitudinal section to the reactor facility 1, have a circular surface with a diameter $d_z$ 7.

Figure 2:
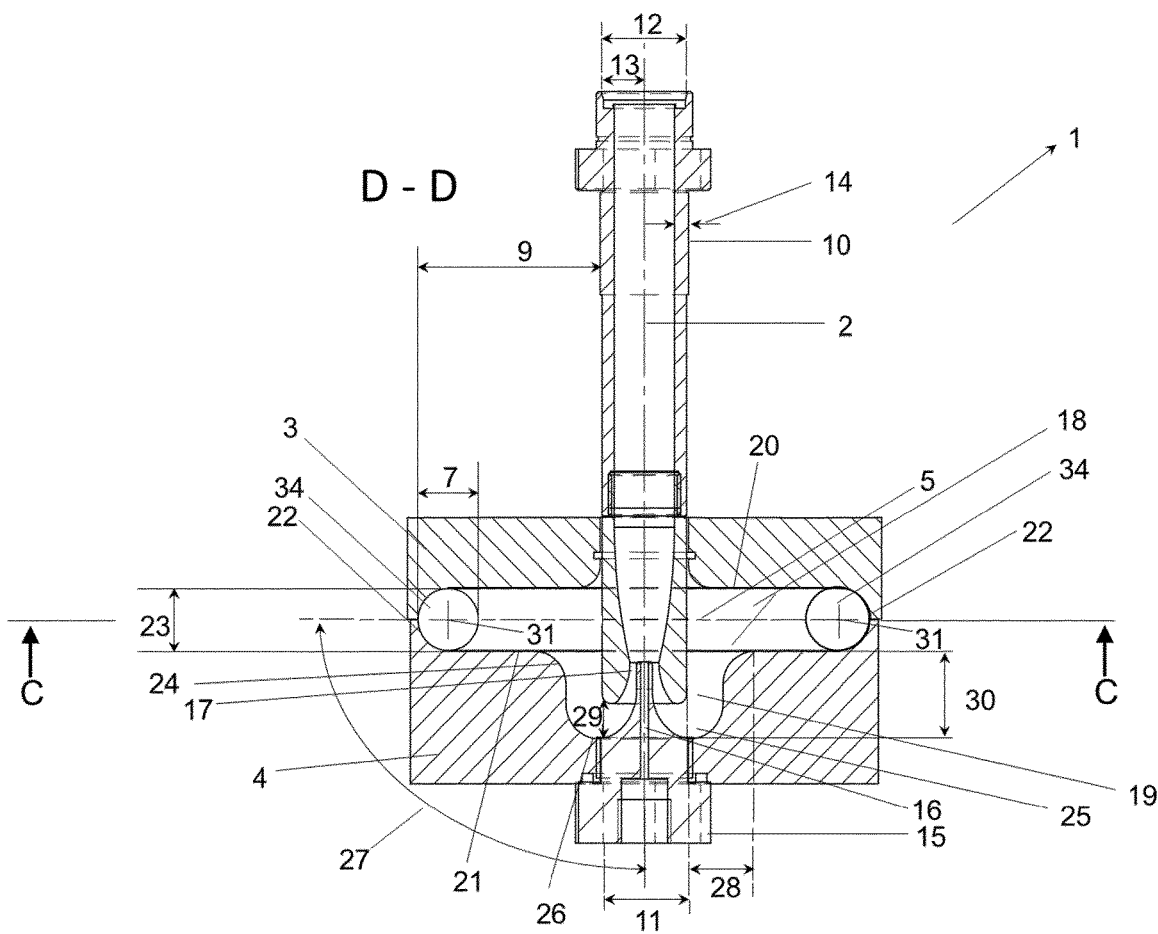
FIG. 2 shows the reactor facility of the invention at a setting angle of α=90° in longitudinal section of the reactor facility along the sectional plane D-D.

FIG. 2 shows the construction of the reactor facility 1 of the invention from the cross section along the plane C-C of FIG. 1 in longitudinal section of the reactor facility 1 along the plane D-D; the components or parts of the reactor facility 1 are located along the longitudinal axis 2. The longitudinal section of the reactor facility 1 along the plane D-D extends in such a way that the fluid inlet region 34 is shown on the left and right sides, in terms of the sectional view in the installed state. The introduced fluid medium flows on the left side out of the sectional plane D-D. In the case of the fluid inlet region 34 on the right side in the sectional view, in turn, the introduced fluid medium flows into the sectional plane D-D. All the features and reference numerals refer to one half of the reactor facility 1 in longitudinal section. Construction of the second half of the reactor facility 1 on the other side of the longitudinal axis 2, however, is the same, since the reactor facility 1 is constructed mirror-symmetrically in longitudinal section.

The reactor facility 1 is split along the center plane 5 into an upper part 3 and a lower part 4 of the housing; the inner walls, in contact with fluid, of the housing 3, 4 form a rotationally symmetrical reaction chamber 18, 19, which likewise has an upper part 18 and a lower part 19. The upper part of the reaction chamber 18 has a top face 20 and a bottom face 21 as well as a transition region from the top to the bottom face 22. The longitudinal axis 2 corresponds to the rotary axis of the rotationally symmetrical reaction chamber 18, 19. There is also an outlet pipe 10 in the reactor facility 1.

The fluid medium is introduced into the upper part of the reaction chamber 18 through a delivery opening (not shown in the longitudinal section) that which is located tangentially in cross section to the jacket face of the upper part of the reaction chamber 18. The delivery opening (not shown in the longitudinal section) is adjoined in the flow direction by a fluid inlet region 34 which, in longitudinal section to the reactor facility 1, has a circular face on the longitudinal section edge that has a diameter $d_z$ 7 and an associated center point 31. The center plane 5 extends through the center point 31 of the fluid inlet region 34. The spacing b 23 between the top face 20 and the bottom face 21 is constant. The setting angle α 27 amounts to 90° and refers to the angle which, viewed in longitudinal section in the installed state, is established relative to the longitudinal axis 2 by the center plane 5, which extends through the center points 31 of the fluid inlet region 34. The setting angle 27 at α=90° refers to an angle, establishing itself in the installed state, below the center plane 5, that is, from the center plane 5 to the longitudinal axis 2 of the reaction chamber 18, 19. For that purpose, the section of the longitudinal axis 2 with the center plane 5 represents a Cartesian coordinate system. The setting angle α 27=90° thus always refers to the third and fourth quadrants of the Cartesian coordinate system. At the setting angle α 27=90° the spacing b 23 is equal to the diameter $d_z$ 7 of the fluid inlet region 34 and is thus equivalent to the height of the upper part of the reaction chamber 18.

The spacing from the transition region from the top face to the bottom face 22 in the upper part of the reaction chamber 18 to the outer wall of the outlet pipe 10 is equivalent to the maximum spacing $r_{max}$ 9 of the upper part of the reaction chamber 18. The fluid-carrying walls of the reaction chamber 18, 19 are such that with regard to their geometry and the surface area, they create a slight friction resistance and coefficient of friction.

The fluid medium is set into rotation in the upper part of the reaction chamber 18 and forms a fluid eddy, which is steered in the flow direction along the longitudinal axis 2 to the lower part of the reaction chamber 19. The lower part of the reaction chamber 19 extends from the transition from the bottom face 24 to a curved floor region 25 that has the lower boundary 26 of the floor region. The radius $r_3$ 28 is equivalent to the spacing from the transition of the bottom face 24 of the lower part of the reaction chamber 19 to the outer wall of the outlet pipe 10. Furthermore, z 30 is equivalent to the spacing of the lower part of the reaction chamber 19, from the point where the top face 20 and the bottom face 21 of the upper part of the reaction chamber 18 no longer have a constant spacing b 23 to one another; z 30 extends as far as the lower boundary 26 of the floor region 25 of the lower part of the reaction chamber 19. In the lower part of the housing 4, a fluid passage 15 shaped as geometrically ascending is located; its longitudinal axis coincides with the longitudinal axis 2 of the reaction chamber 18, 19. The fluid passage has an eversion 16 with a through bore, which protrudes into the location having the smallest free cross section of the inner walls, which are in contact with fluid, of the outlet pipe 10. Through the through bore, additional fluid media can be aspirated as needed into the floor region 25 of the lower part of the reaction chamber 19. The location having the smallest free cross section of the inner walls, on the side in contact with fluid, of the outlet pipe 10 is designed as a nozzle 17 for attaining the Venturi effect 17. The rotating fluid eddy is diverted, while maintaining its speed, at the fluid passage 15 and passes through the inlet opening 11 of the outlet pipe 10 into the outlet pipe 10. The inlet opening 11 is located in the lower part of the reaction chamber 19 and is spaced apart by a variable spacing a 29 from the lower boundary 26 of the curved floor region 25 of the lower part of the reaction chamber 19. Furthermore, the outlet pipe has a radius $r_2$ 13 from the longitudinal axis 2 to the outer wall of the outlet pipe 10 as well as a wall thickness d 14. The fluid medium is carried out of the reactor facility 1 through the outlet opening 12 of the outlet pipe 10.

The fluid-carrying walls of the reaction chamber 18, 19 are such that with regard to their geometry and the surface area they produce a slight friction resistance and coefficient of friction. The requisite pressure for producing the fluid eddy and attaining the Venturi effect in the nozzle 17, with a superimposed negative pressure of ca. −0.99 bar is, because of the slight fluid friction in the reaction chamber 18, 19 of the invention, at 3.5 bar, advantageously ca. 42% lower compared to EP 1 294, which for the same reaction chamber volume requires a pressure of 6.0 bar.

Figure 3:
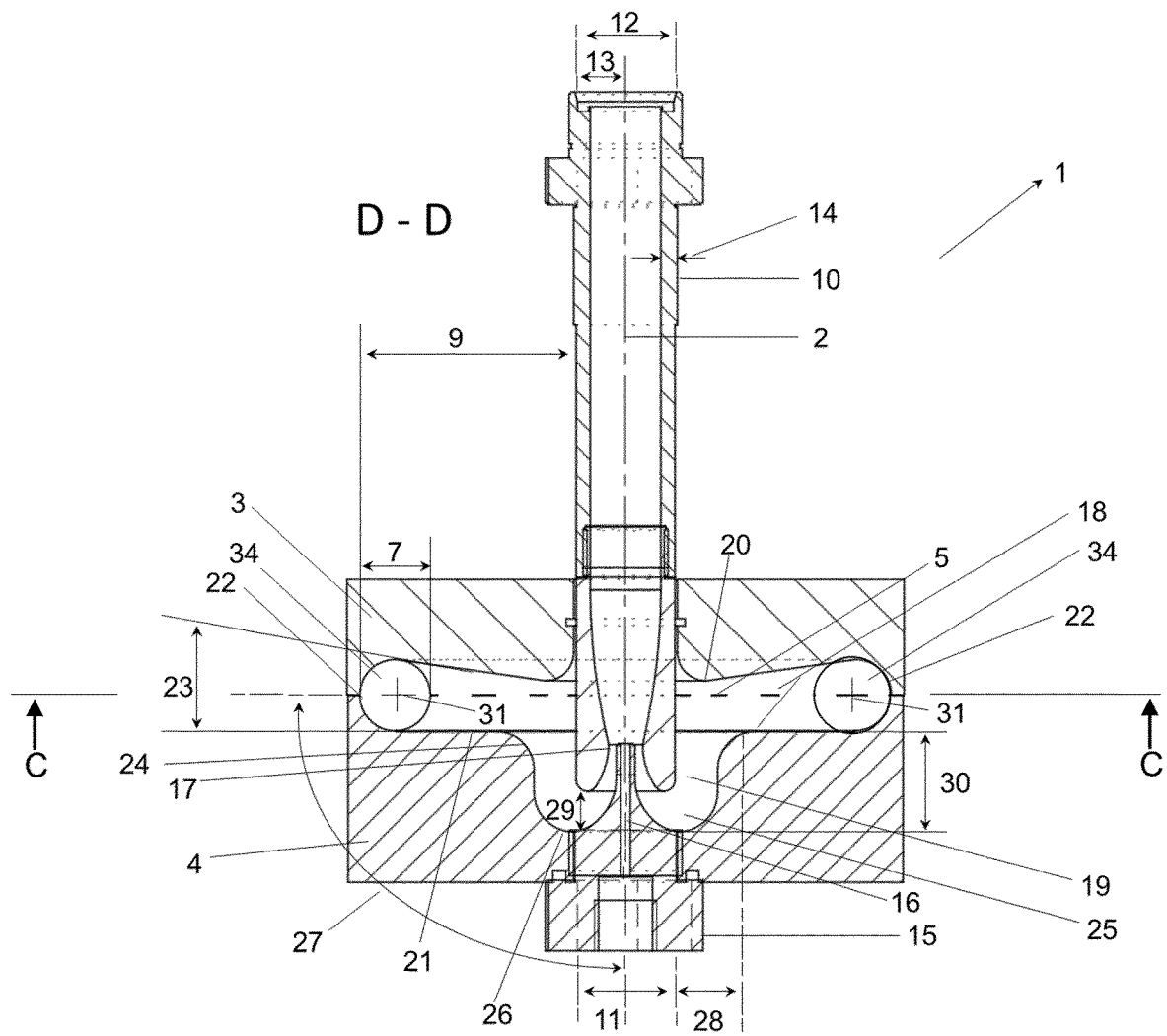
FIG. 3 shows the reactor facility of the invention at a setting angle of α=90° and with a decreasing spacing between the top and bottom face of the upper part of the reaction chamber in longitudinal section of the reactor facility.

FIG. 3 shows the construction of the reactor facility 1 of the invention, from the cross section along the plane C-C of FIG. 1 in the longitudinal section of the reactor facility 1 along the plane D-D; the components or parts of the reactor facility 1 are located along the longitudinal axis 2. The majority of the features of its construction are equivalent to those in the plan view of the cross section in FIGS. 1 and 3, and will therefore not be addressed in further detail.

The setting angle α 27 to the longitudinal axis 2 again amounts to α=90° and refers to the angle that, viewed in longitudinal section in the installed state, is established from the center plane 5, which extends through the center points 31 of the fluid inlet region 34, to the longitudinal axis 2. The spacing b 23 between the top face 20 and the bottom face 21 is maximal ($d_{max}$) in the vicinity of the delivery opening (not shown in the longitudinal section) and of the fluid inlet region 34 and is equivalent to the circular diameter $d_z$ 7 of the fluid inlet region 34. In the flow direction of the fluid medium, the spacing b 23 between the top face 20 and the bottom face 21 to the outer wall of the outlet pipe 10 decreases, as a result of which an additional acceleration of the fluid medium is advantageously achieved.

Figure 4:
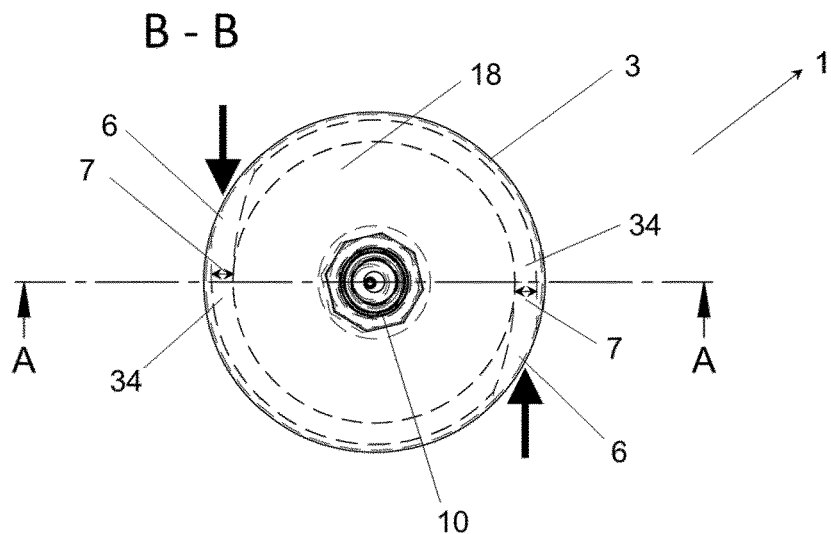
FIG. 4 shows a further plan view, in cross section along the sectional plane B-B, onto the reactor facility of the invention.

FIG. 4 in plan view and cross section along the plane B-B shows the reactor facility 1 of the invention, with the upper part of the housing 3 and the outlet pipe 10. Two inlet pipes (not shown), opposite one another in the longitudinal section of the reactor facility 1 along the plane A-A, discharge in the view along the plane B-B tangentially to the jacket face of the upper part of the reaction chamber 18 and form two delivery openings 6, which in section with the jacket face have an elliptical surface. The two arrows before the respective delivery openings 6 represent the flow direction of the fluid medium. The delivery openings 6 are each adjoined by the fluid inlet regions 34 in the flow direction, which each, in longitudinal section to the reactor facility 1, have a circular surface with a diameter $d_z$ 7.

Figure 5:
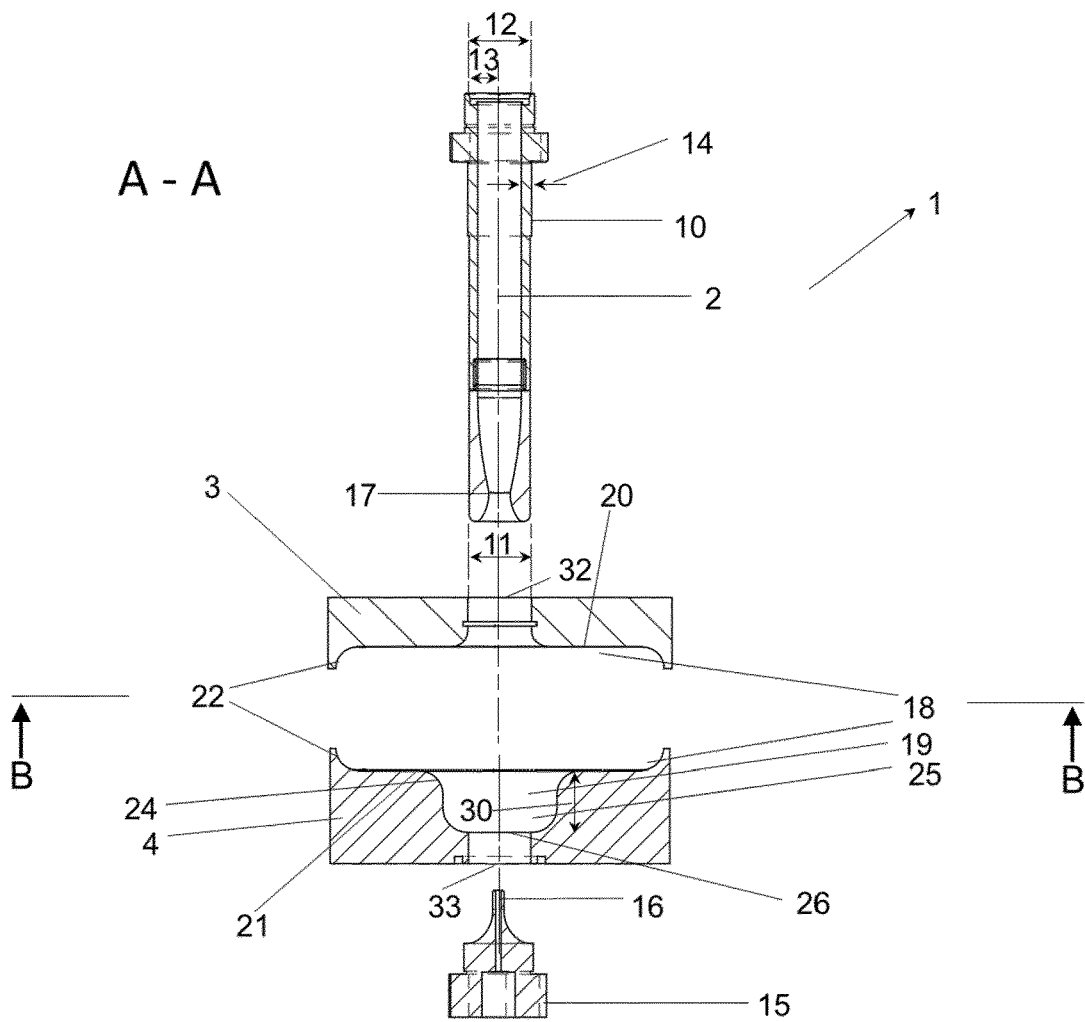
FIG. 5 is an exploded view of the reactor facility of the invention at a setting angle of α=90° in longitudinal section of the reactor facility along the sectional plane A-A.

FIG. 5 in an exploded view shows the components and parts of the reactor facility 1 of the invention from the cross section along the plane B-B of FIG. 3, which are all located along the longitudinal axis 2. In the longitudinal section of the reactor facility 1 along the plane A-A in the installed state, the outlet pipe 10, the upper part of the housing 3 with the upper part of the reaction chamber 18, the lower part of the housing 4 with the lower part of the reaction chamber 19, and the fluid passage 15 with eversion 16 are shown. In the upper part of the housing 3, the opening 32 for the outlet pipe 10 can also be seen; it has the same total cross section as the inlet opening 11 of the outlet pipe 10 and is located adjustably along the longitudinal axis 2. In the lower part of the housing 4, the opening for the fluid passage 33, which is located along the longitudinal axis 2, can also be seen.

The outlet pipe 10 has an inlet opening 11 and an outlet opening 12, as well as a radius $r_2$ 13 from the longitudinal axis 2 to the outer wall of the outlet pipe 10, a wall thickness d 14, and a nozzle for attaining the Venturi effect 17. Also shown for the upper part of the reaction chamber 18 are the top face 20 and the bottom face 21 as well as the transition region from the top face to the bottom face 22. For the lower part of the reaction chamber 19, the transition of the bottom face 24, the floor region 25, the lower boundary 26 of the floor region 25, and the spacing z 30 are shown.

Figure 6:
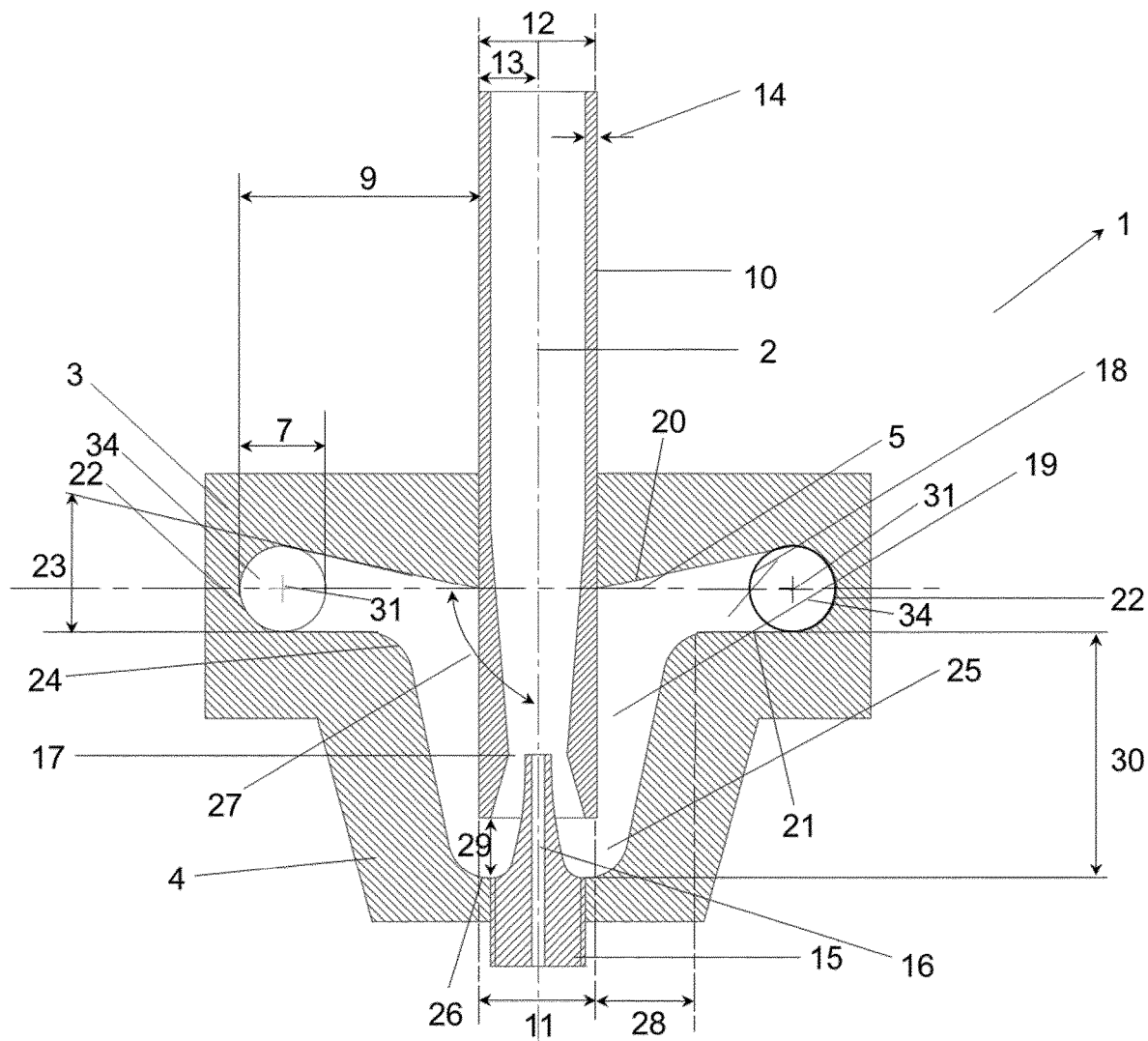
FIG. 6 shows the reactor facility of the invention at a setting angle of α=90° and a decreasing spacing between the top and bottom face of the upper part of the reaction chamber in longitudinal section of the reactor facility.

FIG. 6 shows a further advantageous embodiment of the reactor facility 1 of the invention. The majority of the features of the construction are equivalent to those from the plan view of the cross section in FIG. 1 and FIG. 3, and therefore these will not be further described. The longitudinal section of the reactor facility 1 extends in such a way that the fluid inlet region 34 is shown on what in the sectional view in the installed state are the left- and right sides. The introduced fluid medium flows out of the sectional plane on the left-hand side. In turn, in the case of the fluid inlet region 34 on the right side in the sectional view, the introduced fluid medium flows into the sectional plane.

The setting angle α 27 to the longitudinal axis 2 again amounts to α=90° and refers to the angle which is established relative to the longitudinal axis 2, as viewed in longitudinal section in the installed state, from the center plane 5 that extends through the center points 31 of the fluid inlet region 34. The spacing b 23 between the top face 20 and bottom face 21 is maximal ($b_{max}$) in the vicinity of the delivery opening (not shown in the longitudinal section) and of the fluid inlet region 34 and is equivalent to the circular diameter $d_z$ 7 of the fluid inlet region 34. In the flow direction of the fluid medium, the spacing b 23 between the top face 20 and bottom face 21 to the outer wall of the outlet pipe 10 decreases, as a result of which an additional acceleration of the fluid medium is advantageously attained.

The requisite pressure for generating the fluid eddy and attaining the Venturi effect in the nozzle 17, with a superimposed negative pressure of −0.99 bar, is, because of the lesser fluid friction in the reaction chamber 18, 19, at 5.0 bar, approximately 17% lower compared to EP 1 294 474, which for the same reaction chamber volume requires a pressure of 6.0 bar.

Figure 7:
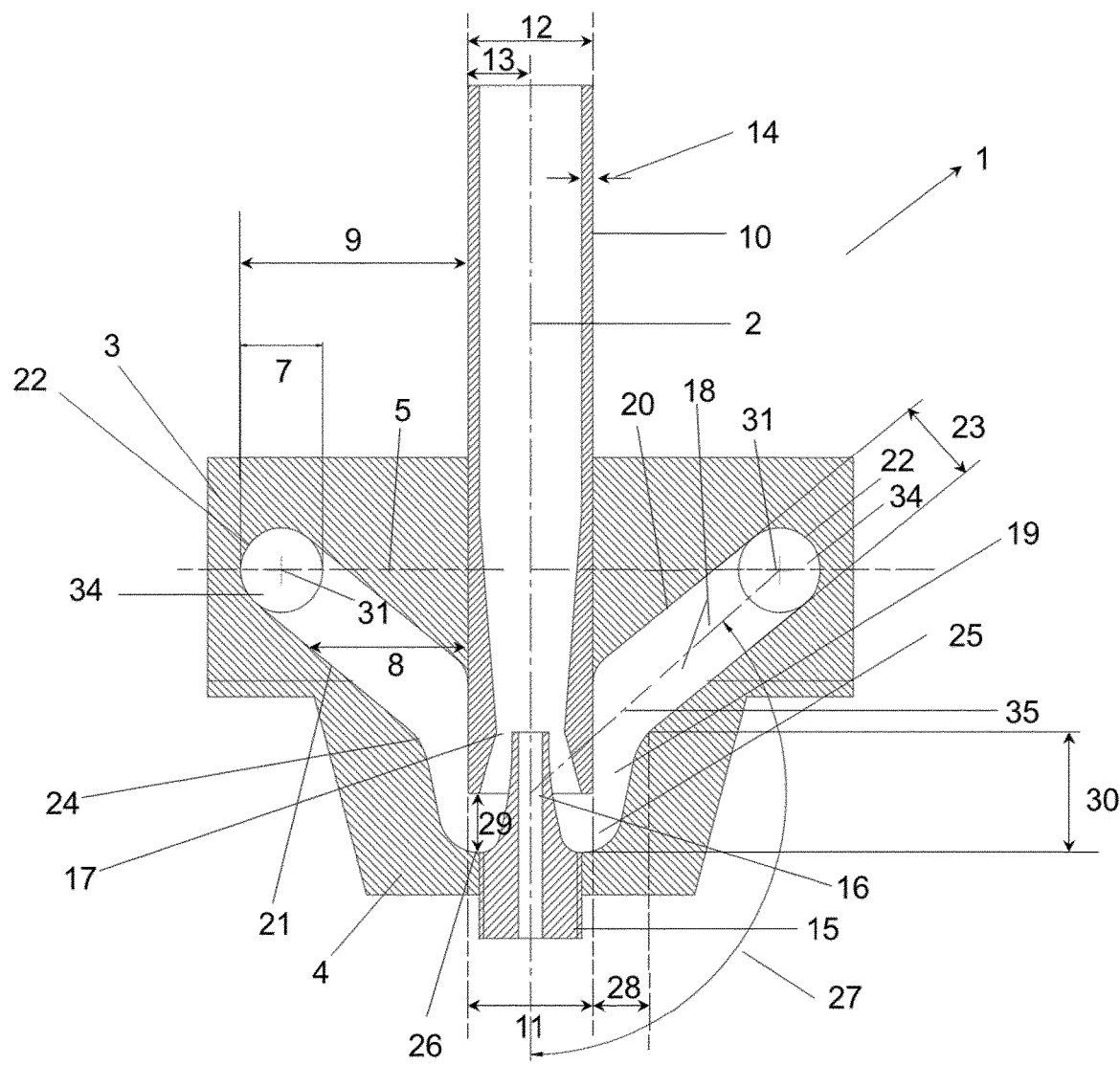
FIG. 7 shows the reactor facility of the invention at a setting angle of α=110° in longitudinal section of the reactor facility.

FIG. 7 shows a further advantageous embodiment of the reactor facility 1 of the invention. The majority of the features of the construction are equivalent to those in the plan view of the cross section in FIGS. 1 and 3, and therefore these will not be further described. The longitudinal section of the reactor facility 1 extends in such a way that the fluid inlet region 34 is shown on the left and right sides in the sectional view in the installed state. The introduced fluid medium flows on the left side out of the sectional plane. In the case of the fluid inlet region 34 on the right side in the sectional view, in turn, the introduced fluid medium flows into the sectional plane.

The spacing b 23 between the top face 20 and the bottom face 21 is constant and is equivalent to the circular diameter $d_z$ 7 of the fluid inlet region 34. The setting angle α 27 to the longitudinal axis 2 amounts to 110°. The setting angle α 27 refers to the angle which, viewed in longitudinal section in the installed state, is established from the imaginary intermediate plane 35, which extends through the respective center points 31 of the fluid inlet region 34 and parallel to the top face 20 of the upper part of the reaction chamber 18. The setting angle α 27=110° refers to the angle, established to the longitudinal axis 2 in the installed state, below the imaginary intermediate plane 35, that is, from the imaginary intermediate plane 35 to the longitudinal axis of the reaction chamber 18, 19.

The radius $r_1$ 8 is equivalent to the spacing from the bottom face 21 of the upper part of the reaction chamber 18 to the outer wall of the outlet pipe 10. In the case where α=110°, $r_1$ 8 in the upper part of the reaction chamber 18 decreases continuously until the transition of the bottom face 24 into the lower part of the reaction chamber 19.

The requisite pressure for generating the fluid eddy and the attainment of the Venturi effect in the nozzle 17 with a superimposed negative pressure of −0.99 bar is approximately 20% lower, because of the lesser fluid friction in the reaction chamber 18, 19 at 4.8 bar, compared to EP 1 294 474, which with identical reaction chamber volumes requires a pressure of 6.0 bar.

LIST OF REFERENCE NUMERALS

1 Reactor facility
2 Longitudinal axis of the reaction chamber
3 Housing, upper part
4 Housing, lower part
5 Center plane
6 Delivery opening
7 Diameter $d_z$ of the fluid inlet region which in the flow direction adjoins the delivery opening, located at a tangent to the upper part of the reaction chamber
8 Radius (spacing of the bottom face of the upper part of the reaction chamber from the outer wall of the outlet pipe)
9 Radius $r_{max}$ (spacing of transition region of the top to the bottom face in the upper part of the reaction chamber from the outer wall of the outlet pipe)
10 Outlet pipe
11 Inlet opening of the outlet pipe (total cross section)
12 Outlet opening of the outlet pipe (total cross section)
13 Radius $r_2$ of the outlet pipe (from the longitudinal axis to the outer wall)
14 Wall thickness d of the outlet pipe
15 Fluid passage
16 Eversion of the fluid passage
17 Nozzle for attaining the Venturi effect
18 Reaction chamber, upper part
19 Reaction chamber, lower part
20 Top face of the upper part of the reaction chamber
21 Bottom face of the upper part of the reaction chamber
22 Transition region from the top face to the bottom face in the upper part of the reaction chamber
23 Spacing b between the top face and the bottom face
4 Transition from the bottom face of the lower part of the reaction chamber
25 Floor region of the lower part of the reaction chamber
26 Lower boundary of the floor region of the lower part of the reaction chamber
27 Setting angle α to the longitudinal axis
28 Radius $r_3$ (spacing from transition of the bottom face of the lower part of the reaction chamber to the outer wall of the outlet pipe)
29 Spacing a between the inlet opening of the outlet pipe and the lower boundary of the lower part of the reaction chamber
30 Spacing z from the bottom face of the lower part of the reaction chamber from the point at which the top face and the bottom face no longer have a constant or decreasing spacing from one another, to the lower boundary of the floor region of the lower part of the reaction chamber
31 Center point of the fluid inlet region
32 Opening in the upper part of the housing for the outlet pipe
33 Opening in the lower part of the housing for the fluid passage
34 Fluid inlet region
35 Imaginary intermediate plane

The invention claimed is:

1. A device in the form of a flow dynamic reactor facility (1) for receiving a fluid medium for producing at least one guided fluid eddy, including a housing (3, 4) and an outlet pipe (10), wherein
the housing (3, 4)
by means of the fluid-contact-side inner walls forms a fluid-carrying hollow chamber, hereinafter called reaction chamber (18, 19), that is rotationally symmetrical about a longitudinal axis (2);
wherein the reaction chamber (18, 19)
is split in the flow direction of the fluid medium into an upper part (18) and a lower part (19)
and the upper part of the reaction chamber (18)
has a top face (20) and a bottom face (21), wherein the top face (20) and/or bottom face (21) have a setting angle to the longitudinal axis (27) of 80° to 115°,
has a transition region from the top face to the bottom face (22),
in the transition region from the top face to the bottom face (22) has a maximum radius (9) referred to the outer wall of the outlet pipe (10),
in the transition region from the top face to the bottom face (22) has at least one delivery opening (6), located tangentially to a jacket face of the upper part of the reaction chamber (18), with a fluid inlet region (34) adjoining it in the flow direction; and
the lower part of the reaction chamber (19)
extends in the flow direction at a spacing z (30) from a transition from the bottom face (24) to a lower boundary of a curved floor region (25), where a geometrically ascending-shaped fluid passage (15) diverts the fluid medium into an inlet opening (11) of the outlet pipe (10); and
the outlet pipe (10) coincides in its longitudinal axis with the longitudinal axis (2) of the rotationally symmetrical reaction chamber (18, 19) and the inlet opening (11) of the outlet pipe (10) is located at a spacing a (29) from what is the lower boundary (26), in the flow direction, of the curved floor region (25).

2. The device of claim 1, characterized in that the outlet pipe (10), in the region near the mouth that adjoins the inlet opening (11), is embodied as a nozzle for producing a Venturi effect (17), and the nozzle for attaining the Venturi effect (17) is designed as a Venturi or a Laval nozzle, and an eversion (16) of the fluid passage (15) ends in the nozzle for attaining the Venturi effect (17).

3. The device of claim 1, characterized in that the fluid inlet region (34) has a diameter $d_z$ (7).

4. The device of claim 1, characterized in that the top face (20) and the bottom face (21) of the upper part of the reaction chamber (18), in the flow direction up to the transition from the bottom face (21) into the lower part of the reaction chamber (19), have a maximally constant or decreasing spacing b (23) from one another, and the spacing b (23) is equivalent to one to three times the diameter $d_z$ (7) of the fluid inlet region (34) (b≤3 $d_z$).

5. The device of claim 1, characterized in that the spacing z (30) amounts to at least half diameter of the fluid inlet region $d_z$ (7) (z≥½ $d_z$).

6. The device of claim 1, characterized in that a radius $r_1$ (8) defines the spacing which extends from the bottom face (21) of the upper part of the reaction chamber (18) to the outer wall of the outlet pipe (10) along a plane parallel to a center plane (5), and a radius $r_3$ (28) defines the spacing that extends from the beginning of the transition of the bottom face (24) of the lower part of the reaction chamber (19) to an outer wall of the outlet pipe (10), where $r_1$ (8) is at least greater than the sum of the diameter of the fluid inlet region $d_z$ (7) and of the spacing $r_3$ (28) ($r_1 \geq d_z + r_3$).

7. The device of claim 1, characterized in that the upper part of the reaction chamber (18) has more than one delivery opening (6) located tangentially to the jacket face of the upper part of the reaction chamber (18).

8. The device of claim 1, characterized in that the outlet pipe (10) and/or the fluid passage (15) is adjustable and shiftable along the longitudinal axis (2).

9. The device of claim 1, characterized in that the fluid passage (15) has a through bore along the longitudinal axis (2).

10. A method for operating a device of claim 1, wherein the fluid medium to be treated is guided in at least one volume flow via the at least one delivery opening (6) into the upper part of the rotationally symmetrical reaction chamber (18) of the housing (3, 4) in such a way that the at least one volume flow is set into a translational and rotary motion along the longitudinal axis (2), which motion is oriented in the flow direction relative to the lower part of the reaction chamber (19), and the at least one volume flow forms a rotating fluid eddy, which in terms of flow technology forms a turbulent boundary layer, so that high centrifugal forces in the fluid eddy arise; and that the fluid eddy is diverted at the fluid passage (15) into the inlet opening (11) of the outlet pipe (10) in what in the installed state is a ascending motion that is opposed to a downward-oriented translational and rotary motion, characterized in that as a result of the flow dynamics treatment of the at least one fluid eddy, the conversion and/or mechanical and physical destruction and/or radicalization of chemical substances or microorganisms found in the fluid medium occurs.

11. The method of claim 10, characterized in that through the through bore along the longitudinal axis (2) in the fluid passage (15), at least one additional fluid medium can be aspirated into the inlet opening (11) of the outlet pipe (10), and it is the same or a different additional fluid medium from the fluid medium that is introduced into the at least one delivery opening (6).

* * * * *